(12) United States Patent
Tanikawa et al.

(10) Patent No.: US 10,259,773 B2
(45) Date of Patent: Apr. 16, 2019

(54) CURABLE COMPOSITION FOR INKJET, AND METHOD FOR MANUFACTURING ELECTRONIC COMPONENT

(71) Applicant: SEKISUI CHEMICAL CO., LTD., Osaka, Osaka (JP)

(72) Inventors: Mitsuru Tanikawa, Osaka (JP); Ryosuke Takahashi, Osaka (JP); Takanori Inoue, Osaka (JP); Michihisa Ueda, Osaka (JP); Tasuku Yamada, Osaka (JP); Yoshito Fujita, Osaka (JP); Takashi Watanabe, Osaka (JP); Yusuke Fujita, Osaka (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 15/526,276

(22) PCT Filed: Feb. 12, 2016

(86) PCT No.: PCT/JP2016/054123
§ 371 (c)(1),
(2) Date: May 11, 2017

(87) PCT Pub. No.: WO2016/129670
PCT Pub. Date: Aug. 18, 2016

(65) Prior Publication Data
US 2017/0298005 A1    Oct. 19, 2017

(30) Foreign Application Priority Data

Feb. 12, 2015 (JP) ................................ 2015-025587
Mar. 18, 2015 (JP) ................................ 2015-055074
Jan. 6, 2016 (JP) ................................ 2016-001206

(51) Int. Cl.
| | | |
|---|---|---|
| *C07C 211/51* | (2006.01) | |
| *C07D 231/12* | (2006.01) | |
| *C07D 249/04* | (2006.01) | |
| *C07D 249/08* | (2006.01) | |
| *C09D 11/101* | (2014.01) | |
| *C09D 11/36* | (2014.01) | |
| *C09D 11/38* | (2014.01) | |
| *H05K 3/28* | (2006.01) | |
| *H05K 1/03* | (2006.01) | |

(52) U.S. Cl.
CPC .......... *C07C 211/51* (2013.01); *C07D 231/12* (2013.01); *C07D 249/04* (2013.01); *C07D 249/08* (2013.01); *C09D 11/101* (2013.01); *C09D 11/36* (2013.01); *C09D 11/38* (2013.01); *H05K 3/287* (2013.01); *H05K 1/0346* (2013.01); *H05K 2203/013* (2013.01)

(58) Field of Classification Search
CPC .................. C07C 211/51; H05K 3/287; H05K 2203/013; H05K 1/0346; C09D 11/38; C09D 11/101; C09D 11/36; C07D 249/08; C07D 249/04; C07D 231/12
USPC ......................................... 522/170, 168, 144
See application file for complete search history.

(56) References Cited

U.S. PATENT DOCUMENTS

| | | | | |
|---|---|---|---|---|
| 4,943,516 A | * | 7/1990 | Kamayachi | G03F 7/027 427/177 |
| 5,702,820 A | * | 12/1997 | Yokoshima | C08F 290/064 427/510 |
| 7,462,653 B2 | * | 12/2008 | Kakinuma | C09D 11/101 430/269 |
| 2006/0058412 A1 | | 3/2006 | Kakinuma | |
| 2008/0124456 A1 | | 5/2008 | Satou et al. | |
| 2013/0208064 A1 | * | 8/2013 | Ueda | B41M 5/0023 347/102 |
| 2016/0046813 A1 | * | 2/2016 | Tanikawa | C09D 4/00 428/413 |
| 2016/0233615 A1 | * | 8/2016 | Scholeno | H01R 12/712 |
| 2017/0233599 A1 | * | 8/2017 | Tanikawa | C09J 5/06 257/777 |

FOREIGN PATENT DOCUMENTS

| | | |
|---|---|---|
| EP | 2 902 455 A1 | 8/2015 |
| EP | 3 249 024 A1 | 11/2017 |
| JP | 2008-133336 A | 6/2008 |
| JP | 2010-37456 A | 2/2010 |
| JP | 2012-92312 A | 5/2012 |
| JP | 2012-153924 A | 8/2012 |
| JP | 2012-184411 A | 9/2012 |
| JP | 2012-184412 A | 9/2012 |

(Continued)

OTHER PUBLICATIONS

International Search Report for the Application No. PCT/JP2016/054123 dated May 17, 2016.

(Continued)

*Primary Examiner* — Sanza L. McClendon
(74) *Attorney, Agent, or Firm* — Cheng Law Group, PLLC

(57) ABSTRACT

Provided is a curable composition for inkjet which can have a prolonged pot life even under an environment in an inkjet device that is warmed to 50° C. or higher and which can be cured into a cured product having improved heat resistance and insulation reliability, in spite of the fact that a thermally curable compound is used in the curable composition. The curable composition for inkjet according to the present invention contains a photocurable compound, a thermally curable compound, a photopolymerization initiator and a thermal curing agent and does not contain a solvent or contains the solvent, wherein the content of the solvent in 100% by weight of the curable composition is 1% by weight or less when the curable composition for inkjet contains the solvent, the photocurable compound contains a polyfunctional compound having at least two (meth)acryloyl groups, and the thermal curing agent is an aromatic amine having at least one benzene ring and at least two amino groups.

16 Claims, No Drawings

(56) References Cited

FOREIGN PATENT DOCUMENTS

| JP | 2014-237814 A | 12/2014 | |
|---|---|---|---|
| KR | 10-2009-0013750 A | 2/2009 | |
| KR | 10-2012-0062682 A | 6/2012 | |
| WO | WO-2004/099272 A1 | 11/2004 | |
| WO | WO-2012039379 A1 * | 3/2012 | .......... B41M 5/0023 |
| WO | WO-2014/050688 A1 | 4/2014 | |

OTHER PUBLICATIONS

Written Opinion of the International Searching Authority (PCT/ISA/237) for Application No. PCT/JP2016/054123 dated May 17, 2016.
Korean Office Action for the Application 10-2017-7001066 dated Jul. 20, 2017.
Written Opinion of the International Searching Authority (PCT/ISA/237 for Application No. PCT/JP2016/054123 dated May 17, 2016 (English Translation dated Aug. 24, 2017).
Supplementary European Search Report for the Application No. 16 749 313.9 dated Mar. 21, 2018.

* cited by examiner

CURABLE COMPOSITION FOR INKJET, AND METHOD FOR MANUFACTURING ELECTRONIC COMPONENT

TECHNICAL FIELD

The present invention relates to a curable composition for inkjet which is applied with an inkjet device upon use and which is irradiated with light to make the curing thereof proceed and is subsequently cured by heating upon use. The present invention also relates to a method for manufacturing an electronic component having a cured product layer formed from the curable composition for inkjet.

BACKGROUND ART

Heretofore, many printed wiring boards have been used, in each of which a solder resist pattern, which is a pattern-shaped solder resist film, is formed on a substrate having a wiring provided on the upper surface thereof. In the printed wiring boards, finer solder resist patterns have been demanded with the reduced sizes of electronic devices and the increased densities of the patterns in electronic devices.

As the method for forming a fine solder resist pattern, a method in which a solder resist composition is applied by an inkjet mode has been proposed. In an inkjet mode, the number of steps is reduced compared with the case where a solder resist pattern is formed in a screen printing mode. Therefore, in an inkjet mode, a solder resist pattern can be formed easily and highly efficiently.

In the case where a solder resist composition is applied by an inkjet mode, it is required that the viscosity of the solder resist composition is low to a certain extent during the application of the solder resist composition. Recently, on the other hand, an inkjet device that can be warmed to 50° C. or higher during printing has been developed. When a solder resist composition is warmed to 50° C. or higher in an inkjet device, the viscosity of the solder resist composition can become relatively low, and therefore the dischargeability of the solder resist composition with the inkjet device can be further improved.

A solder resist composition that can be applied by an inkjet mode is disclosed in Patent Document 1. In Patent Document 1, a curable composition for inkjet which comprises a monomer having both a (meth)acryloyl group and a thermally curable functional group, a photoreactive diluent having a weight average molecular weight of 700 or less and a photopolymerization initiator is disclosed. The viscosity of the curable composition for inkjet at 25° C. is 150 mPa·s or less.

RELATED ART DOCUMENT

Patent Document

Patent Document 1: WO2004/099272A1

SUMMARY OF THE INVENTION

Problems to be Solved by the Invention

The viscosity of the curable composition for inkjet disclosed in Patent Document 1 is relatively low. Therefore, the curable composition for inkjet disclosed in Patent Document 1 can be applied onto a substrate by an inkjet mode.

However, the curable composition for inkjet disclosed in Patent Document 1 contains a monomer having both a (meth)acryloyl group and a thermally curable functional group, and therefore has a problem that the pot life of the curable composition under an environment having a temperature of 50° C. or higher is short.

For example, in the case where a curable composition for inkjet is to be discharged with an inkjet device, the curable composition for inkjet generally remains in the inkjet device for a certain period of time after the curable composition is supplied into the inkjet device. On the other hand, for the purpose of improving the dischargeability of the curable composition, the inside of the inkjet device is sometimes warmed to 50° C. or higher. With respect to the curable composition for inkjet disclosed in Patent Document 1, the curing of the composition often proceeds in the inside of the inkjet device which is warmed to 50° C. or higher and consequently the viscosity of the composition may increase, resulting in the difficulty in discharge of the composition.

In addition, the conventional curable compositions for inkjet have a problem that the heat resistance and insulation reliability of cured products after curing of the curable compositions, are poor.

An object of the present invention is to provide a curable composition for inkjet which can be applied by an inkjet mode, can have a prolonged pot life even under an environment in an inkjet device which is warmed to 50° C. or higher in spite of a fact that a thermally curable compound is used in the curable composition, and can be cured into a cured product having improved heat resistance and insulation reliability. Another object of the present invention is to provide a method for manufacturing an electronic component using the curable composition for inkjet.

Means for Solving the Problems

According to a broad aspect of the present invention, a curable composition for inkjet is provided, which is applied with an inkjet device upon use and is irradiated with light to make the curing thereof proceed and is subsequently cured by heating upon use, wherein the curable composition comprises a photocurable compound, a thermally curable compound, a photopolymerization initiator and a thermal curing agent, and containing no solvent or containing a solvent, the content of the solvent is 1% by weight or less in 100% by weight of the curable composition for inkjet when the curable composition contains the solvent, the photocurable compound contains a polyfunctional compound having at least two (meth)acryloyl groups, and the thermal curing agent is an aromatic amine having at least one benzene ring and at least two amino groups.

The aromatic amine is preferably an aromatic amine represented by formula (1) or formula (2) shown below.

[Chemical formula 1]

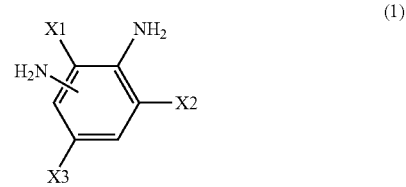

In formula (1), X1, X2 and X3 independently represent an alkyl group having 1 to 6 carbon atoms or an SCH$_3$ group.

[Chemical formula 2]

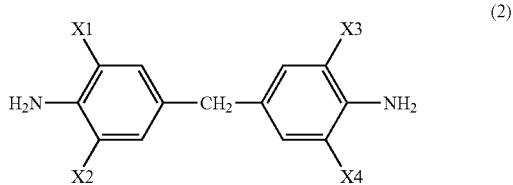

(2)

In formula (2), X1, X2, X3 and X4 independently represent an alkyl group having 1 to 6 carbon atoms or an $SCH_3$ group.

The curable composition for inkjet according to the present invention preferably contains an aromatic heterocyclic compound having a 5-membered ring containing a nitrogen atom.

In a specific aspect of the curable composition for inkjet according to the present invention, the aromatic heterocyclic compound is a compound represented by formula (3), formula (4) or formula (5) shown below.

[Chemical formula 3]

(3)

[Chemical formula 4]

(4)

[Chemical formula 5]

(5)

In a specific aspect of the curable composition for inkjet according to the present invention, the viscosity of the curable composition as measured before heating at 25° C. in accordance with JIS K2283 is 160 to 1200 mPa·s inclusive and the ratio of the viscosity of the curable composition as measured after heating at 80° C. for 24 hours under an oxygen-free environment to the above-mentioned viscosity of the curable composition as measured before heating is 1.1 or less.

The curable composition for inkjet according to the present invention preferably contains a color material.

The curable composition for inkjet according to the present invention is used suitably for forming a solder resist film.

According to another broad aspect of the present invention, a method for manufacturing an electronic component is provided, which comprises the steps of: applying a curable composition for inkjet as mentioned above by an inkjet mode to draw a pattern with the curable composition; and irradiating the pattern-shaped curable composition for inkjet with light and then applying heat to the pattern-shaped curable composition to cure the pattern-shaped curable composition, thereby forming a cured product layer.

Effect of the Invention

The curable composition for inkjet according to the present invention comprises a photocurable compound, a thermally curable compound, a photopolymerization initiator and a thermal curing agent and does not contain a solvent or contains the solvent, wherein the content of the solvent is 1% by weight or less in 100% by weight of the curable composition when the curable composition for inkjet contains the solvent, the photocurable compound contains a polyfunctional compound having at least two (meth)acryloyl groups, and the thermal curing agent is an aromatic amine having both at least one benzene ring and at least two amino groups. Therefore, the pot life of the curable composition can be prolonged even under an environment in an inkjet device which is warmed to 50° C. or higher in spite of a fact that a thermally curable compound is used in the curable composition. Furthermore, the heat resistance and insulation reliability of a cured product of the curable composition for inkjet according to the present invention, which is produced by curing the curable composition, can be improved.

MODE(S) FOR CARRYING OUT THE INVENTION

Hereinbelow, the details about the present invention will be described.

(Curable Composition for Inkjet)

The curable composition for inkjet according to the present invention (sometimes abbreviated to "a curable composition", hereinafter) is applied with an inkjet device upon use. The curable composition according to the present invention is different from a curable composition which is to be applied by screen printing, and a curable composition to be applied with a dispenser or the like.

The curable composition according to the present invention is irradiated with light to make the curing of the curable composition proceed and is subsequently cured by heating upon use. The curable composition according to the present invention is a photocurable and thermally curable composition, and has both photocurability and thermal curability. The curable composition according to the present invention is different from a curable composition which can be cured only with light, and a curable composition which can be cured only with heat or the like.

The curable composition according to the present invention comprises a photocurable compound (A), a photopolymerization initiator (B), a thermally curable compound (C) and a thermal curing agent (D). The curable composition according to the present invention does not contain a solvent (F) or contains the solvent (F). The curable composition according to the present invention may contain the solvent (F) or may not contain the solvent (F). When the curable composition according to the present invention contains the solvent (F), the content of the solvent (F) is 1% by weight or less in 100% by weight of the curable composition. Therefore, when the curable composition according to the present invention contains the solvent (F), it is preferred that the content of the solvent (F) be small. The curable composition according to the present invention may contain a color material (G). The curable composition according to the present invention may contain an aromatic heterocyclic compound (H) having a 5-membered ring containing a nitrogen atom.

In the curable composition according to the present invention, the photocurable compound (A) comprises a polyfunctional compound having at least two (meth)acryloyl groups.

In the curable composition according to the present invention, the thermal curing agent (D) is an aromatic amine having both at least one benzene ring and at least two amino groups.

Since the curable composition according to the present invention has the above-mentioned constitution, the pot life of the curable composition can be prolonged even under an environment in an inkjet device which is warmed to 50° C. or higher in spite of a fact that the thermally curable compound (C) is used in the curable composition, and the heat resistance and insulation reliability of a cured product produced by curing the curable composition can be improved.

Since the curable composition according to the present invention contains the photocurable compound (A) and the photopolymerization initiator (B), a resist pattern which is a cured product of the curable composition can be produced by irradiating the curable composition with light to produce a primary cured product and then applying the heat to the primary cured product to cure the curable composition. In this manner, the wetting/spread of the curable composition which is applied on a member of interest, such as a substrate, can be prevented by performing the primary curing by the irradiation with light. Consequently, a fine resist pattern can be formed with high precision.

The curable composition according to the present invention contains the thermally curable compound (C) and the thermal curing agent (D). Since the activity of the thermal curing agent (D) is significantly low at a temperature lower than a temperature at which the thermal curing agent (D) becomes active, the thermal curability is inhibited. As a result, the pot life can be sufficiently prolonged even under an environment in an inkjet device which is warmed to 50° C. or higher in spite of a fact that the thermally curable compound (C) is used in the curable composition. In the curable composition which is not applied yet by an inkjet mode, the viscosity is rarely increased even when warmed to 50° C. or higher, and therefore the thermal curing is less likely to proceed. For these reasons, the curable composition has excellent stability under an environment in an inkjet device which is warmed to 50° C. or higher and can be discharged through an inkjet nozzle stably. Consequently, it becomes possible to form a uniform resist pattern. Even when the thermal curing agent (D) is used, the curing of the curable composition can proceed satisfactorily when the curable composition is cured by heating to a relatively high temperature.

Since the curable composition according to the present invention contains particularly the thermally curable compound (C), the heat resistance of a cured product produced by curing the curable composition can be improved.

With respect to the curable composition, the viscosity $\eta 1$ as measured at 25° C. and 2.5 rpm in accordance with JIS K2283 is preferably 160 mPa·s or more and is preferably 1200 mPa·s or less. When the viscosity $\eta 1$ of the curable composition is equal to or more than the above-mentioned lower limit and equal to or less than the above-mentioned upper limit, the curable composition can be discharged through an inkjet head easily and with high precision. In addition, even when the curable composition is warmed to 50° C. or higher, the composition can be discharged through an inkjet head easily and with high precision.

The viscosity $\eta 1$ is more preferably 1000 mPa·s or less, still more preferably 500 mPa·s or less. When the viscosity satisfies the preferred above-mentioned upper limit, the dischargeability of the curable composition becomes better when the curable composition is discharged continuously through an inkjet head. In addition, from the viewpoint of further prevention of the wetting/spread of the curable composition and the further improvement in resolution of a cured product layer to be formed, it is preferred that the viscosity $\eta 1$ be more than 500 mPa·s.

Hereinbelow, details about each of the components contained in the curable composition for inkjet according to the present invention will be described.

[Photocurable Compound (A)]

For the purpose of curing the curable composition by irradiation with light, the curable composition contains a photocurable compound (A). The photocurable compound (A) contains a bifunctional or higher (meth)acrylate. The photocurable compound contains a polyfunctional compound (A1) having at least two (meth)acryloyl groups (a polyfunctional photocurable compound) as an essential component, and may additionally contain a monofunctional compound (A2) having one (meth)acryloyl group (a monofunctional photocurable compound).

Specific examples of the bifunctional or higher photocurable compound, among the components for the photocurable compound (A), include 1,4-butanediol di(meth)acrylate, 1,3-butanediol di(meth)acrylate, 1,6-hexanediol di(meth)acrylate, 1,9-nonanediol di(meth)acrylate, 1,10-decanediol di(meth)acrylate, 2-n-butyl-2-ethyl-1,3-propanediol di(meth)acrylate, dipropylene glycol di(meth)acrylate, tripropylene glycol di(meth)acrylate, polypropylene glycol di(meth)acrylate, ethylene glycol di(meth)acrylate, diethylene glycol di(meth)acrylate, tetraethylene glycol di(meth)acrylate, polyethylene glycol di(meth)acrylate, propylene oxide-added bisphenol A di(meth)acrylate, ethylene oxide-added bisphenol A di(meth)acrylate, ethylene oxide-added bisphenol F di(meth)acrylate, dimethylol dicyclopentadiene di(meth)acrylate, 1,3-butylene glycol di(meth)acrylate, neopentyl glycol di(meth)acrylate, ethylene oxide-modified isocyanuric acid di(meth)acrylate, 2-hydroxy-3-(meth)acryloyloxypropyl (meth)acrylate, carbonate diol di(meth)acrylate, polyether diol di(meth)acrylate, polyester diol di(meth)acrylate, polycaprolactone diol di(meth)acrylate, polybutadiene diol di(meth)acrylate, pentaerythritol tri(meth)acrylate, trimethylolpropane tri(meth)acrylate, propylene oxide-added trimethylolpropane tri(meth)acrylate, ethylene oxide-added trimethylolpropane tri(meth)acrylate, caprolactone-modified trimethylolpropane tri(meth)acrylate, ethylene oxide-added isocyanuric acid tri(meth)acrylate, dipentaerythritol penta(meth)acrylate, dipentaerythritol hexa(meth)acrylate, ditrimethylolpropane tetra(meth)acrylate, pentaerythritol tetra(meth)acrylate, glycerin tri(meth)acrylate, propylene oxide-added glycerin tri(meth)acrylate, and tris (meth)acryloyl oxyethyl phosphate.

Specific examples of the monofunctional photocurable compound, among the components for the photocurable compound (A), include 2-hydroxyethyl acrylate, 2-hydroxypropyl (meth)acrylate, 4-hydroxybutyl (meth)acrylate, 2-hydroxybutyl (meth)acrylate, isobutyl (meth)acrylate, t-butyl (meth)acrylate, isooctyl (meth)acrylate, lauryl (meth)acrylate, stearyl (meth)acrylate, isobornyl (meth)acrylate, cyclohexyl (meth)acrylate, 2-methoxyethyl (meth)acrylate, methoxyethylene glycol (meth)acrylate, 2-ethoxyethyl (meth)acrylate, tetrahydrofurfuryl (meth)acrylate, benzyl (meth)acrylate, ethylcarbitol (meth)acrylate, phenoxyethyl (meth)acrylate, phenoxydiethylene glycol (meth)acrylate, phenoxypolyethylene glycol (meth)acrylate, methoxypolyethylene glycol (meth)acrylate, 2,2,2-trifluoroethyl (meth) acrylate, 2,2,3,3-tetrafluoropropyl (meth)acrylate, 1H,1H, 5H-octafluoropentyl (meth)acrylate, imide (meth)acrylate, methyl (meth)acrylate, ethyl (meth)acrylate, n-butyl (meth)

acrylate, propyl (meth)acrylate, n-butyl (meth)acrylate, cyclohexyl (meth)acrylate, 2-ethylhexyl (meth)acrylate, n-octyl (meth)acrylate, isononyl (meth)acrylate, isomyristyl (meth)acrylate, 2-butoxyethyl (meth)acrylate, 2-phenoxyethyl (meth)acrylate, bicyclopentenyl (meth)acrylate, isodecyl (meth)acrylate, diethylaminoethyl (meth)acrylate, dimethylaminoethyl (meth)acrylate, 2-(meth)acryloyloxyethyl succinic acid, 2-(meth)acryloyloxyethyl hexahydrophthalic acid, 2-(meth)acryloyloxyethyl-2-hydroxypropyl phthalate, glycidyl (meth)acrylate and 2-(meth)acryloyloxyethyl phosphate.

The term "(meth)acrylate" refers to an acrylate or a methacrylate. The term "(meth)acryloyl" refers to an acryloyl or a methacryloyl.

The content of the photocurable compound (A) is not particularly limited. The content of the photocurable compound (A) in 100% by weight of the curable composition is preferably 10% by weight or more, more preferably 20% by weight or more, and is preferably 90% by weight or less, more preferably 85% by weight or less.

From the viewpoint of further improvement in curability with light, it is preferred that the polyfunctional compound (A1) having at least two (meth)acryloyl groups contain a polyfunctional compound having at least two acryloyl groups. From the viewpoint of still further improvement in curability with light, it is more preferred that the photocurable compound (A) contain a polyfunctional compound having at least three (meth)acryloyl groups.

The content of the polyfunctional compound (A1) having at least two (meth)acryloyl groups is not particularly limited. The content of the polyfunctional compound (A1) having at least two (meth)acryloyl groups in 100% by weight of the curable composition is preferably 10% by weight or more, more preferably 20% by weight or more, and is preferably 90% by weight or less, more preferably less than 90% by weight, still more preferably 80% by weight or less, particularly preferably less than 80% by weight.

[Photopolymerization Initiator (B)]

For the purpose of curing the curable composition by irradiation with light, the curable composition contains a photopolymerization initiator (B) together with the photocurable compound (A). Specific examples of the photopolymerization initiator (B) include a photo-radical polymerization initiator and photo-cationic polymerization initiator. The photopolymerization initiator (B) is preferably a photo-radical polymerization initiator. These photopolymerization initiators (B) may be used singly, or two or more of them may be used in combination.

The photo-radical polymerization initiator is not particularly limited. The photo-radical polymerization initiator is a compound which can generate radicals upon the irradiation with light to initiate a radical polymerization reaction. Specific examples of the photo-radical polymerization initiator include benzoin, benzoin alkyl ethers, acetophenones, aminoacetophenones, anthraquinones, thioxanthones, ketals, 2,4,5-triarylimidazole dimer, riboflavin tetrabutyrate, a thiol compound, 2,4,6-tris-s-triazine, an organic halogen compound, benzophenones, xanthones and 2,4,6-trimethylbenzoyldiphenylphosphine oxide. These photo-radical polymerization initiators may be used singly, or two or more of them may be used in combination.

Specific examples of the benzoin alkyl ethers include benzoin methyl ether, benzoin ethyl ether and benzoin isopropyl ether. Specific examples of the acetophenones include acetophenone, 2,2-dimethoxy-2-phenylacetophenone, 2,2-diethoxy-2-phenylacetophenone and 1,1-dichloroacetophenone. Specific examples of the aminoacetophenones include 2-methyl-1-[4-(methylthio)phenyl]-2-morpholinopropan-1-one, 2-benzyl-2-dimethylamino-1-(4-morpholinophenyl)-butan-1-one and N,N-dimethylaminoacetophenone. Specific examples of the anthraquinones include 2-methylanthraquinone, 2-ethylanthraquinone, 2-t-butylanthraquinone and 1-chloroanthraquinone. Specific examples of the thioxanthones include 2,4-dimethyl thioxanthone, 2,4-diethyl thioxanthone, 2-chlorothioxanthone and 2,4-diisopropylthioxanthone. Specific examples of the ketals include acetophenone dimethyl ketal and benzyl dimethyl ketal. Specific examples of the thiol compound include 2-mercaptobenzimidazole, 2-mercaptobenzoxazole and 2-mercaptobenzothiazole. Specific examples of the organic halogen compound include 2,2,2-tribromoethanol and tribromomethylphenylsulfone. Specific examples of the benzophenones include benzophenone and 4,4'-bisdiethylaminobenzophenone.

It is possible to use a photopolymerization initiation aid together with the photo-radical polymerization initiator. Specific examples of the photopolymerization initiation aid include N,N-dimethylaminobenzoic acid ethyl ester, N,N-dimethylaminobenzoic acid isoamyl ester, pentyl-4-dimethylaminobenzoate, triethylamine and triethanolamine. A photopolymerization initiation aid other than the above-mentioned compounds may also be used. These photopolymerization initiation aids may be used singly, or two or more of them may be used in combination.

It is also possible to use a titanocene compound, such as CGI-784 and the like (manufactured by Ciba Specialty Chemicals) of which the absorption occurs in a visible light region, or the like for the purpose of promoting the photoreaction.

The photo-cationic polymerization initiator is not particularly limited, and specific examples thereof include a sulfonium salt, a iodonium salt, a metallocene compound, benzoin tosylate and the like. These photo-cationic polymerization initiators may be used singly, or two or more of them may be used in combination.

[Thermally Curable Compound (C)]

The curable composition contains a thermally curable compound (C) so that the curable composition can be cured by heating. The use of a thermally curable compound (C) enables the further curing of the curable composition or a primary cured product of the curable composition by the application of heat. The use of a thermally curable compound (C) also enables the efficient and highly precise formation of a resist pattern and the improvement in heat resistance and insulation reliability of the cured product. Only one type of the thermally curable compound may be used, or two or more types of the thermally curable compounds may be used in combination.

From the viewpoint of improvement in curability and production of a cured product having further improved heat resistance and insulation reliability, the thermally curable compound (C) is preferably a compound having a cyclic ether group. Specific examples of the cyclic ether group include an epoxy group and an oxetanyl group. Among these groups, the cyclic ether group is preferably an epoxy group from the viewpoint of improvement in curability and the production of a cured product having further improved heat resistance and insulation reliability. It is preferred that the compound having a cyclic ether group have at least two cyclic ether groups.

Specific examples of the compound having an epoxy group include a bisphenol S-type epoxy compound, a diglycidyl phthalate compound, a heterocyclic epoxy compound (e.g., triglycidyl isocyanurate), a bixylenol-type epoxy compound, a biphenol-type epoxy compound, a tetraglycidyl xylenoyl ethane compound, a bisphenol A-type epoxy compound, a hydrogenated bisphenol A-type epoxy compound, a bisphenol F-type epoxy compound, a brominated bisphenol A-type epoxy compound, a phenol novolac-type epoxy compound, a cresol novolac-type epoxy compound, an alicyclic epoxy compound, a novolac-type epoxy compound of bisphenol A, a chelate-type epoxy compound, a glyoxal-type epoxy compound, an amino group-containing epoxy compound, a rubber-modified epoxy compound, a dicyclopentadiene phenolic-type epoxy compound, a silicone-modified epoxy compound and an ε-caprolactone-modified epoxy compound.

Specific examples of the compound having an oxetanyl group are mentioned in, for example, Japanese Patent No. 3074086.

It is preferred that the viscosity of the thermally curable compound (C) at 25° C. be more than 300 mPa·s.

The amount of the thermally curable compound (C) to be added is adjusted appropriately in such a manner that the curable composition can be cured properly by the application of heat, and is not particularly limited. The content of the thermally curable compound (C) in 100% by weight of the curable composition is preferably 3% by weight or more, more preferably 5% by weight or more, still more preferably 10% by weight or more, and is preferably 80% by weight or less, more preferably 75% by weight or less. When the content of the thermally curable compound (C) is equal to or more than the above-mentioned lower limit, it becomes possible to more effectively cure the curable composition by the application of heat. When the content of the thermally curable compound (C) is equal to or less than the above-mentioned upper limit, the heat resistance of the cured product can be further improved.

[Thermal Curing Agent (D)]

The curable composition contains a thermal curing agent (D) so that the curable composition can be cured more efficiently by the application of heat. The thermal curing agent (D) can cure the thermally curable compound (C). The thermal curing agent (D) is an aromatic amine having both at least one benzene ring and at least two amino groups. Only one type of the thermal curing agent (D) may be used, or two or more types of the thermal curing agents (D) may be used in combination. From the viewpoint of prolongation of the pot life of the curable composition, it is preferred that the thermal curing agent (D) be a latent thermal curing agent.

Specific examples of the thermal curing agent (D) include α,α'-bis(4-aminophenyl)-p-diisopropylbenzene, diaminodiethyldimethyldiphenylmethane, diaminodiphenylsulfone, diaminodiphenylmethane, 4,4'-diaminodiphenylether, methaphenylenediamine, diethyltoluenediamine, α-(m/p-aminophenyl)ethylamine, m-xylenediamine, dimethylthiotoluenediamine, 1,3-bis[2-(4-aminophenyl)-2-propyl]benzene, and α,α'-bis(4-aminophenyl)-1,4-diisopropylbenzene.

From the viewpoint of improvement in cooling/heating cycle reliability, it is preferred that the aromatic amine be an aromatic amine represented by formula (1) or formula (2) shown below.

[Chemical formula 6]

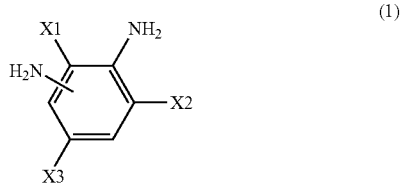

(1)

In formula (1), X1, X2 and X3 independently represent an alkyl group having 1 to 6 carbon atoms or an SCH$_3$ group.

[Chemical formula 7]

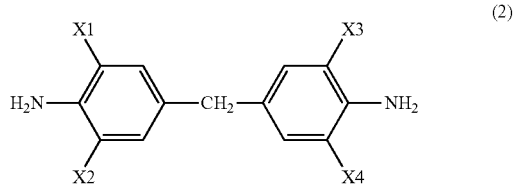

(2)

In formula (2), X1, X2, X3 and X4 independently represent an alkyl group having 1 to 6 carbon atoms or an SCH$_3$ group.

Specifically, the thermal curing agent (D) is preferably diethyltoluenediamine, dimethylthiotoluenediamine or diaminodiethyldimethyldiphenylmethane. These preferred thermal curing agents may be used singly, or two or more of them may be used in combination.

The thermal curing agent (D) may be one capable of curing the curable composition at a heating temperature of 100° C. or higher, or may be one cable of curing the curable composition at a heating temperature of 120° C. or higher.

The compounding ratio of the thermally curable compound (C) to the thermal curing agent (D) is not particularly limited. The amount of the thermal curing agent (D) to be added is adjusted appropriately in such a manner that the curable composition can be cured properly by the application of heat, and is not particularly limited. The content of the thermal curing agent (D) in 100 parts by weight of the thermally curable compound (C) is preferably 5 parts by weight or more, more preferably 10 parts by weight or more, and is preferably 60 parts by weight or less, more preferably 50 parts by weight or less.

[Adhesiveness-imparting Agent (E)]

It is preferred that the curable composition contain an adhesiveness-imparting agent (E). When the curable composition contains an adhesiveness-imparting agent (E), the acid resistance of the cured product can be further improved.

Specific examples of the adhesiveness-imparting agent (E) include an imidazole-based adhesiveness-imparting agent, a thiazole-based adhesiveness-imparting agent, a triazole-based adhesiveness-imparting agent, a pyrazole-based adhesiveness-imparting agent, and a silane coupling agent. The adhesiveness-imparting agent (E) is preferably a triazole-based adhesiveness-imparting agent or a pyrazole-based adhesiveness-imparting agent. It is preferred that the curable composition contain a triazole compound or a pyrazole compound. The triazole compound has a triazole skeleton. The pyrazole compound has a pyrazole skeleton.

Preferred examples of the triazole-based adhesiveness-imparting agent and the pyrazole-based adhesiveness-imparting agent include 1,2,4-triazole, 4-amino-1,2,4-triazole, 1,2,3-triazole, 3-mercapto-1,2,4-triazole, 1-[N,N-bis(2-ethylhexyl)aminomethyl]benzotriazole, 1-[N,N-bis(2-ethylhexyl)aminomethyl]methylbenzotriazole, 2,2'-[[(methyl-1H-benzotriazole-1-yl)methyl]imino]bisethanol, pyrazole, 3-amino-5-tert-butylpyrazole, 1-allyl-3,5-dimethylpyrazole, 3-aminopyrazole, and 3,5-dimethylpyrazole.

From the viewpoint of further improvement in acid resistance of the cured product, it is preferred that the adhesiveness-imparting agent (E) contain an aromatic heterocyclic compound having a 5-membered ring containing a nitrogen atom. In other words, from the viewpoint of further improvement in acid resistance of the cured product, it is preferred that the curable composition contain an aromatic heterocyclic compound having a 5-membered ring containing a nitrogen atom.

From the viewpoint of still further improvement in acid resistance of the cured product, it is preferred that the aromatic heterocyclic compound be a compound represented by formula (3), formula (4) or formula (5) shown below.

[Chemical formula 8]

(3)

[Chemical formula 9]

(4)

[Chemical formula 10]

(5)

From the viewpoint of still further improvement in acid resistance of the cured product, the content of the adhesiveness-imparting agent (E) in 100% by weight of the curable composition is preferably 0.1% by weight or more. From the viewpoint of further improvement in the pot life of the curable composition, the content of the adhesiveness-imparting agent (E) in 100% by weight of the curable composition is preferably 3% by weight or less.

[Solvent (F)]

The curable composition does not contain a solvent (F) or contains the solvent (F). The curable composition may contain the solvent (F) or may contain no solvent (F). When the curable composition contains the solvent (F), the content of the solvent (F) in 100% by weight of the curable composition is 1% by weight or less. From the viewpoint of more highly precise formation of the curable composition layer and further reduction in possibility of the formation of voids in the curable composition layer, it is preferred that the content of the solvent (F) in the curable composition be as small as possible.

Specific examples of the solvent (F) include water and an organic solvent. Among these solvents, from the viewpoint of further improvement in removability of residual materials, an organic solvent is preferred. Specific examples of the organic solvent include: alcohols such as ethanol; ketones such as acetone, methyl ethyl ketone and cyclohexanone; aromatic hydrocarbons such as toluene, xylene and tetramethylbenzene; glycol ethers such as cellosolve, methyl cellosolve, butyl cellosolve, carbitol, methyl carbitol, butyl carbitol, propylene glycol monomethyl ether, dipropylene glycol monomethyl ether, dipropylene glycol diethyl ether and tripropylene glycol monomethyl ether; esters such as ethyl acetate, butyl acetate, ethyl lactate, butyl lactate, cellosolve acetate, butyl cellosolve acetate, carbitol acetate, butyl carbitol acetate, propylene glycol monomethyl ether acetate, dipropylene glycol monomethyl ether acetate and propylene carbonate; aliphatic hydrocarbons such as octane and decane; and a petroleum-based solvent such as petroleum ether and naphtha.

When the curable composition contains the solvent (F), the content of the solvent (F) in 100% by weight of the curable composition is preferably 0.5% by weight or less.

[Color Material (G)]

The curable composition may contain a color material (G). The color material (G) is preferably a dye. Only one type of the color material (G) may be used, or two or more types of the color materials (G) may be used in combination.

Specific examples of the color material (G) include a phthalocyanine-based compound, an anthraquinone-based compound, an azo-based compound, a nigrosine-based compound and a perylene-based compound.

From the viewpoint of improvement in storage stability and curability of the curable composition, it is preferred that the color material (G) be a phthalocyanine-based compound, an anthraquinone-based compound or a nigrosine-based compound.

Specific examples of the phthalocyanine-based compound include copper phthalocyanine and iron phthalocyanine. Specific examples of the anthraquinone-based compound include alizarin and dihydroxyanthraquinone. Specific examples of the azo-based compound include p-(phenylazo) phenol and 1,5-dioxynaphthalene.

Examples of commercially available products of the phthalocyanine-based compound include 650M, valifast 2610, valifast 2620, valifast blue 1605 and valifast blue 2670 which are manufactured by Orient Chemical Industries Co., Ltd. An example of a commercially available product of the anthraquinone-based compound is NUBIAN BLUE PS-5630 which is manufactured by Orient Chemical Industries Co., Ltd. Examples of commercially available products of the azo-based compound include valifest black 3804, valifest black 3820 and valifest black 3870 which are manufactured by Orient Chemical Industries Co., Ltd. An example of a commercially available product of the nigrosine-based compound is valifest black 1821 which is manufactured by Orient Chemical Industries Co., Ltd.

The amount of the color material (G) to be added is adjusted appropriately in such a manner that the cured product can have a desired color, and is not particularly limited. The content of the color material (G) in 100% by weight of the curable composition is preferably 0.01% by weight or more and is preferably 5% by weight or less.

[Other Components]

From the viewpoint of heat resistance, it is preferred that the curable composition contain a curing accelerator. Specific examples of the curing accelerator include a tertiary amine, an imidazole, a quaternary ammonium salt, a quaternary phosphonium salt, an organic metal salt, a phosphorus compound and a urea-based compound. These curing accelerators may be used singly, or two or more of them may be used in combination.

The content of the curing accelerator in 100% by weight of the curable composition is preferably 0.01% by weight or more, more preferably 0.1% by weight or more, and is preferably 10% by weight or less, more preferably 5% by weight or less.

In the curable composition, various types of additives may be added as long as the objects of the present invention are not hindered. The types of the additives are not particularly limited, and an antifoaming agent, a leveling agent and the like can be mentioned as examples of the additives.

Specific examples of the antifoaming agent include a silicone-based antifoaming agent, a fluorine-containing antifoaming agent and a polymer-based antifoaming agent. Specific examples of the leveling agent include a silicone-based leveling agent, a fluorine-containing leveling agent and a polymer-based leveling agent.

[Method for Manufacturing Electronic Component]

Next, a method for manufacturing an electronic component according to the present invention will be described.

In the method for manufacturing an electronic component according to the present invention, the above-mentioned curable composition for inkjet is used. That is, in the method for manufacturing an electronic component according to the present invention, the curable composition is firstly applied by an inkjet mode to draw a pattern. In this regard, it is particularly preferred to directly draw a pattern with the curable composition. The term "directly draw" refers to drawing a pattern without the use of a mask. Examples of the electronic component include a printed wiring board and a touch panel component. The electronic component is preferably a wiring board, more preferably a printed wiring board (a printed substrate).

For the application of the curable composition, an inkjet printer is used. The inkjet printer has an inkjet head. The inkjet head has a nozzle. It is preferred that the inkjet device be provided with a warming unit for warming the inside of the inkjet device or the inside of the inkjet head to 50° C. or higher. It is preferred that the curable composition be applied onto a member of interest. An example of the member of interest is a substrate. An example of the substrate is a substrate having a wiring or the like provided on the upper surface thereof. It is preferred that the curable composition be applied onto a printed wiring board.

It is also possible to manufacture a glass substrate for use in a display device, e.g., a liquid crystal display device, by using a member mainly composed of a glass in place of the substrate in the method for manufacturing an electronic component according to the present invention. Specifically, it is possible to form a conductive pattern, e.g., an ITO pattern, on a glass by a technique such as vapor deposition and then form a cured product layer on the conductive pattern by an inkjet mode by the method for manufacturing an electronic component according to the present invention. In this regard, when patterns are formed with a conductive ink or the like on the cured product layer, the cured product layer becomes an insulating film and it becomes possible to achieve electric connection between predetermined patterns among the conductive patterns on the glass.

Subsequently, the pattern-shaped curable composition is irradiated with light and then heat is applied to the pattern-shaped curable composition to cure the pattern-shaped curable composition, thereby forming a cured product layer. In this manner, an electronic component having a cured product layer can be manufactured. The cured product layer may be an insulating film or a resist pattern. The insulating film may be a pattern-like insulating film. The cured product layer is preferably a resist pattern. The resist pattern is preferably a solder resist pattern.

The method for manufacturing an electronic component according to the present invention is preferably a method for manufacturing a printed wiring board having a resist pattern. In this regard, it is preferred that the curable composition be applied by an inkjet mode to draw a pattern with the curable composition, then the pattern-shaped curable composition be irradiated with light, and then heat be applied to the pattern-shaped curable composition to be cured, thereby forming the resist pattern.

It is also possible to irradiate the pattern-shaped curable composition with light to cause the primary curing of the curable composition, thereby producing a primary cured product. In this case, the wetting/spread of the pattern-shaped curable composition can be prevented, and consequently it becomes possible to form a highly precise resist pattern. When the primary cured product is produced by the irradiation with light, it is also possible to apply heat to the primary cured product to cure the primary cured product to produce a cured product, thereby forming the cured product layer such as a resist pattern. The curable composition according to the present invention can be cured by both the irradiation with light and the application of heat. When the curing with light and the curing with heat are employed in combination, it becomes possible to form a cured product layer, e.g., a resist pattern, which has further improved heat resistance. The heating temperature to be employed for the curing by the application of heat is preferably 100° C. or higher, more preferably 120° C. higher, and is preferably 250° C. or lower, more preferably 200° C. or lower.

The irradiation with light may be carried out after the drawing of the pattern or simultaneously with the drawing of the pattern. For example, the irradiation with light may be carried out simultaneously with or immediately after the discharge of the curable composition. In order to irradiate the curable composition with light simultaneously with the drawing of the pattern, it is possible to place a light source in such a manner that a site at which the curable composition is to be irradiated with light can coincident with a site at which the pattern is to be drawn with the curable composition.

The light source to be employed for the irradiation with light can be selected appropriately depending on light to be emitted. Examples of the light source include an UV-LED, a low-pressure mercury lamp, a medium-pressure mercury lamp, a high-pressure mercury lamp, an ultrahigh-pressure mercury lamp, a xenon lamp and a metal halide lamp. The light to be emitted is generally ultraviolet ray, or may be electron beam, α ray, β ray, γ ray, X ray, neutron ray or the like.

The temperature at which the curable composition is to be applied is not particularly limited, as long as the viscosity of the curable composition can become such a level that the curable composition can be discharged through an inkjet head. The temperature at which the curable composition is to be applied is preferably 50° C. or higher, more preferably 60° C. or higher, and is preferably 100° C. or lower. The viscosity of the curable composition during the application of the curable composition is not particularly limited, as long as the curable composition can be discharged through an inkjet head.

It is also possible to employ a method in which the substrate is cooled during printing. In the case where the substrate is cooled, the viscosity of the curable composition upon the landing of the curable composition on the substrate is increased, leading to the improvement in resolution. In this case, it is preferred that the cooling be carried out to such an extent that dew formation does not occur, or the atmospheric air be dehumidified so as to prevent the occurrence of dew formation. In this case, since the cooling can cause the shrinkage of the substrate, the dimensional precision of the substrate may be corrected.

Since the above-mentioned specific compound is used as the thermal curing agent (D), the pot life of the curable composition can be prolonged sufficiently and the stable discharge of the curable composition can be achieved even when, for example, the curable composition is heated in an inkjet head. In addition, since the curable composition can be heated to a viscosity suitable for the application by an inkjet mode, it becomes possible to suitably manufacture an electronic component such as a printed wiring board by using the curable composition according to the present invention.

Hereinbelow, the present invention will be described specifically with reference to Examples and Comparative Examples. However, the present invention is not intended to be limited only to Examples mentioned below.

EXAMPLE 1

Tricyclodecane dimethanol diacrylate ("IRR214-K" manufactured by DAICEL-ALLNEX LTD.) (70 parts by weight) which corresponds to a polyfunctional compound (A1) having at least two (meth)acryloyl groups, an α-aminoalkylphenone-type photo-radical polymerization initiator ("Irgacure 907" manufactured by BASF Japan Ltd.) (5 parts by weight) which corresponds to a photopolymerization initiator (B), a bisphenol A-type epoxy resin ("YD-127" manufactured by NIPPON STEEL & SUMIKIN CHEMICAL CO., LTD.) (15 parts by weight) which corresponds to a thermally curable compound (C), and dimethylthiotoluenediamine ("EH105L" manufactured by ADEKA CORPORATION) (10 parts by weight) which corresponds to a thermal curing agent (D) were mixed together to produce a curable composition for inkjet.

EXAMPLES 2 To 89 AND COMPARATIVE EXAMPLES 1 TO 12

The same procedure as in Example 1 was carried out, except that the types and amounts of the ingredients to be added are changed to those shown in Tables 1 to 18. In this manner, curable compositions for inkjet were produced.

In Examples 46 to 84, the following adhesiveness-imparting agents (E) were used.
(Pyrazole Compounds)
Pyrazole
3-Amino-5-tert-butylpyrazole
1-Allyl-3,5-dimethylpyrazole
3-Aminopyrazole
3,5-Dimethylpyrazole
(Triazole Compounds)
1,2,4-Triazole
4-Amino-1,2,4-triazole
1,2,3-Triazole
3-Mercapto-1,2,4-triazole
1-[N,N-Bis(2-ethylhexyl)aminomethyl]benzotriazole
1-[N,N-Bis(2-ethylhexyl)aminomethyl]methylbenzotriazole
2,2'-[[(Methyl-1H-benzotriazole-1-yl)methyl]imino]bisethanol
(Imidazole Compounds)
Benzimidazole
1-Methylbenzimidazole
1,2-Dimethylimidazole
1-Benzyl-2-methylimidazole
1-Benzyl-2-phenylimidazole
1-Cyanoethyl-2-methylimidazole
1-Cyanoethyl-2-ethyl-4-methylimidazole
(Evaluation)
(1) Viscosity The viscosity η1 of each of the curable compositions was measured immediately after the preparation thereof, at 25° C. and 2.5 rpm with a viscometer ("TVE22L" manufactured by Toki Sangyo Co., Ltd.) in accordance with JIS K2283. The viscosity η1 of each of the curable compositions was evaluated by the following evaluation criteria.

[Evaluation Criteria for Viscosity]
A: The viscosity η1 was more than 1200 mPa·s.
B: The viscosity η1 was more than 1000 mPa·s and not more than 1200 mPa·s.
C: The viscosity η1 was more than 500 mPa·s and not more than 1000 mPa·s.
D: The viscosity η1 was not less than 160 mPa·s and not more than 500 mPa·s.
E: The viscosity η1 was less than 160 mPa·s.

(2) Increase in Viscosity (Storage Stability and Length of Pot Life)

The viscosity η1 of each of the curable compositions was measured immediately after the preparation thereof, at 25° C. and 2.5 rpm with a viscometer ("TVE22L" manufactured by Toki Sangyo Co., Ltd.) in accordance with JIS K2283. Next, each of the curable compositions which were obtained immediately after the preparation thereof was heated 80° C. for 24 hours. The viscosity η2 of each of the heated curable composition was measured in the same manner as for the viscosity η1. The increase in viscosity was evaluated by the following evaluation criteria. In this test, the heating was carried out in an oxygen-free environment.

[Evaluation Criteria for Increase in Viscosity]
○○: The (η2/η1) ratio was not less than 1 and not more than 1.1.
○: The (η2/η1) ratio was more than 1.1 and not more than 1.2.
Δ: The (η2/η1) ratio was more than 1.2 and not more than 1.3.
x: The (η2/η1) ratio was more than 1.3.

(3) Inkjet Dischargeability

The test for the dischargeability of each of the curable compositions was carried out through an inkjet head of a piezo inkjet printer equipped with an ultraviolet ray irradiation device, and the inkjet dischargeability was evaluated by the evaluation criteria mentioned below. The head temperature was adjusted to 80° C. in the test for the dischargeability of a curable composition having a viscosity of 500 mPa·s or less, and the head temperature was adjusted to 95° C. in the test for the dischargeability of a curable composition having a viscosity of more than 500 mPa·s.

[Evaluation Criteria for Inkjet Dischargeability]
○○: The curable composition could be discharged continuously for 10 hours or longer through the head.
○: The curable composition could be discharged continuously for 10 hours or longer through the head, but slight discharge non-uniformity was observed during the continuous discharge for 10 hours.
Δ: The curable composition could be discharged through the head continuously, but could not be discharged continuously for 10 hours or longer.
x: The curable composition could not be discharged through the head in an initial stage.

(4) Wettability/Spreadability

A copper foil-attached FR-4 substrate in which a copper foil was adhered onto the upper surface was provided. Each of the curable compositions was discharged and applied in the form of lines having a line width of 80 μm and a line-line distance of 80 μm onto the substrate through an inkjet head of a piezo inkjet printer equipped with an ultraviolet ray irradiation device in such a manner that the entire surface of the copper foil was coated with the curable composition, thereby drawing a pattern with each of the curable compositions. The head temperature was adjusted to 80° C. in the test for the dischargeability of a curable composition having a viscosity of 500 mPa·s or less, and the head temperature was adjusted to 95° C. in the test for the dischargeability of a curable composition having a viscosity of more than 500 mPa·s.

The curable composition (thickness 20 μm) applied onto the substrate was irradiated with ultraviolet ray having a wavelength of 365 nm at an irradiation energy of 1000 mJ/cm$^2$.

Five minutes after the irradiation with ultraviolet ray, the wetting/spread of the pattern was observed visually, and the wetting/spread was evaluated by the following criteria.

[Evaluation Criteria for Wetting/Spread]

◯◯: The wetting/spread was in such a state that the line width was the desired line width+40 μm or less.

◯: The wetting/spread was in such a state that the line width was more than the desired line width+40 μm and was the desired line width+75 μm or less.

x: The composition layer was wetting/spread from the drawn part, wherein the line-line distance was lost or the wetting/spread was in such a state that the line width was more than the desired line width+75 μm.

(5) Length of Pot Life

Each of the curable composition was filtrated through a 5-μm membrane filter, and the filtrated curable composition was heated at 80° C. for 24 hours.

A copper foil-attached FR-4 substrate in which a copper foil was adhered onto the upper surface was provided. It is tried to draw a pattern by discharging and applying each of the curable compositions in the form of lines having a line width of 80 μm and a line-line distance of 80 μm onto the copper foil on the substrate through an inkjet head of a piezo inkjet printer equipped with an ultraviolet ray irradiation device. The length of the pot life was evaluated by the following evaluation criteria on the basis of the dischargeability through the inkjet head. The head temperature was adjusted to 80° C. in the test for the dischargeability of a curable composition having a viscosity of 500 mPa·s or less, and the head temperature was adjusted to 95° C. in the test for the dischargeability of a curable composition having a viscosity of more than 500 mPa·s.

[Evaluation Criteria for Length of Pot Life]

◯◯: The composition could be discharged through the inkjet head.

◯: The curing of the composition slightly proceeded or the viscosity of the composition was slightly increased before the discharge of the composition, but the composition could be discharged through the inkjet head.

Δ: The composition was cured or the viscosity of the composition was increased before the discharge of the composition, and therefore the composition could not be discharged through the inkjet head.

x: The composition was considerably cured.

(6) Heat Resistance

A copper foil-attached FR-4 substrate in which a copper foil was adhered onto the upper surface was provided. A pattern was drawn by discharging and applying each of the curable compositions in the form of lines having a line width of 80 μm and a line-line distance of 80 μm onto the copper foil on the substrate through an inkjet head of a piezo inkjet printer equipped with an ultraviolet ray irradiation device. The head temperature was adjusted to 80° C. in the test for the dischargeability of a curable composition having a viscosity of 500 mPa·s or less, and the head temperature was adjusted to 95° C. in the test for the dischargeability of a curable composition having a viscosity of more than 500 mPa·s.

The pattern-shaped curable composition (thickness 20 μm) was irradiated with ultraviolet ray having a wavelength of 365 nm at an irradiation energy of 1000 mJ/cm$^2$ using a high-pressure mercury lamp to produce a primary cured product. Subsequently, the primary cured product was heated at 150° C. for 60 minutes to cure the primary cured product, thereby producing a resist pattern that was a cured product.

The laminate of the substrate and the resist pattern thus produced was heated in an oven having a temperature of 270° C. for 5 minutes, and then the appearance of the heated resist pattern was checked visually. In addition, a cellophane tape was attached onto the heated resist pattern and then the cellophane tape was detached in the 90-degree direction. The heat resistance was evaluated by the appearance test and the delamination test by the following criteria.

[Evaluation Criteria for Heat Resistance]

◯: The resist pattern was not changed before and after the heating in the appearance test, and the resist pattern was not delaminated from the substrate in the delamination test.

x: At least one phenomenon selected from cracking, delamination and swelling of the resist pattern was observed in the appearance test, or the resist pattern was delaminated from the substrate in the delamination test.

(7) Acid Resistance

A copper foil-attached FR-4 substrate in which a copper foil was adhered onto the upper surface was provided. A pattern was drawn by discharging and applying each of the curable compositions in the form of lines having a line width of 80 μm and a line-line distance of 80 μm onto the copper foil on the substrate through an inkjet head of a piezo inkjet printer equipped with an ultraviolet ray irradiation device. The head temperature was adjusted to 80° C. in the test for the dischargeability of a curable composition having a viscosity of 500 mPa·s or less, and the head temperature was adjusted to 95° C. in the test for the dischargeability of a curable composition having a viscosity of more than 500 mPa·s.

The pattern-shaped curable composition (thickness 20 μm) was irradiated with ultraviolet ray having a wavelength of 365 nm at an irradiation energy of 1000 mJ/cm$^2$ using a high-pressure mercury lamp to produce a primary cured product. Subsequently, the primary cured product was heated at 150° C. for 60 minutes to cure the primary cured product, thereby producing a resist pattern that was a cured product.

The laminate of the substrate and the resist pattern thus produced was immersed in a 10 wt %-aqueous hydrochloric acid solution, and the acid resistance was evaluated from the time until the occurrence of delamination of the resist pattern by the following criteria.

[Evaluation Criteria for Acid Resistance]

◯◯: The delamination of the resist pattern was not observed even when the laminate was immersed in the aqueous hydrochloric acid solution for 30 minutes or longer.

○: The time until the occurrence of delamination was 20 minutes or longer and was shorter than 30 minutes.

Δ: The time until the occurrence of delamination was 10 minutes or longer and was shorter than 20 minutes.

×: The time until the occurrence of delamination was shorter than 10 minutes.

(8) Insulation Reliability (Migration Resistance)

An IPC-B-25 comb-shaped test pattern B was provided. The comb-shaped test pattern B was warmed to 80° C., and then each of the curable compositions was discharged and applied through an inkjet head of a piezo inkjet printer equipped with an ultraviolet ray irradiation device in such a manner that the entire surface of the comb-shaped test pattern B could be coated. The head temperature was adjusted to 80° C. in the test for the dischargeability of a curable composition having a viscosity of 500 mPa·s or less, and the head temperature was adjusted to 95° C. in the test for the dischargeability of a curable composition having a viscosity of more than 500 mPa·s.

The applied curable composition (thickness 20 μm) was irradiated with ultraviolet ray having a wavelength of 365 nm at an irradiation energy of 1000 mJ/cm$^2$ using a high-pressure mercury lamp to produce a primary cured product. Subsequently, the primary cured product was heated at 150° C. for 60 minutes to cure the primary cured product, thereby producing a resist pattern that was a cured product. In this manner, test pieces were produced.

Each of the test pieces thus produced was subjected to a humidification test for 500 hours under the conditions of a temperature of 85° C., a relative humidity of 85% and the application of a direct current of 50 V. The insulation resistance after the humidification test was measured. The insulation reliability was evaluated by the following criteria.

[Evaluation Criteria for Insulation Reliability]

○: The insulation resistance became 10$^{10}$Ω or more after the elapse of 500 hours.

Δ: The criterion "○" was not applicable, and the insulation resistance value became 10$^{10}$Ω or more after the elapse of 250 hours.

×: The insulation resistance became less than 10$^{10}$Ω before the elapse of 250 hours.

(9) Long-Term Reliability (Evaluation of Cooling/Heating Cycle Resistance)

A copper foil-attached FR-4 substrate in which a copper foil was adhered onto the upper surface was provided. A pattern was drawn by discharging and applying each of the curable compositions in the form of lines having a line width of 80 μm and a line-line distance of 80 μm onto the copper foil on the substrate through an inkjet head of a piezo inkjet printer equipped with an ultraviolet ray irradiation device. The head temperature was adjusted to 80° C. in the test for the dischargeability of a curable composition having a viscosity of 500 mPa·s or less, and the head temperature was adjusted to 95° C. in the test for the dischargeability of a curable composition having a viscosity of more than 500 mPa·s.

The pattern-shaped curable composition (thickness 20 μm) was irradiated with ultraviolet ray having a wavelength of 365 nm at an irradiation energy of 1000 mJ/cm$^2$ using a high-pressure mercury lamp to produce a primary cured product. Subsequently, the primary cured product was heated at 160° C. for 60 minutes to cure the primary cured product, thereby producing a resist pattern that was a cured product.

The laminate of the substrate and the resist pattern thus produced was subjected to a cooling/heating cycle test using a liquid chamber-type thermal shock tester ("TSB-51" manufactured by ESPEC), wherein one cycle comprised retaining the laminate at −40° C. for 5 minutes, then heating the laminate to 120° C., then retaining the laminate at 120° C. for 5 minutes, and then cooling the laminate to −40° C. Samples were collected from the laminate respectively after 500 cycles and 1000 cycles.

The samples were observed with a stereo microscope ("SMZ-10" manufactured by Nikon Corporation). The observation was carried out to determine whether or not cracking occurred in the resist pattern or whether or not the resist pattern was delaminated from the substrate in each of the samples. The cooling/heating cycle resistance property was evaluated by the following criteria.

[Evaluation Criteria for Cooling/Heating Cycle Resistance]

○: Cracking was not observed in a resist pattern and the resist pattern was not delaminated from the substrate.

Δ: Slight cracking was observed in a resist pattern or the resist pattern was delaminated from the substrate slightly, but these phenomena were not critical for practical use.

×: Significant cracking was observed in the resist pattern or the resist pattern was significantly delaminated from the substrate, and these phenomena were critical for practical use.

The details and the results are shown in Tables 1 to 18 shown below. In the evaluations other than the evaluations on (1) viscosity and (2) increase in viscosity (storage stability and length of pot life), curable compositions which were not heated at 80° C. for 24 hours were used.

TABLE 1

| | Product No. | | Manufacturer |
|---|---|---|---|
| Component (A1), bifunctional or higher | IRR214-K | Tricyclodecane dimethanol diacrylate | Daicel-Allnex Ltd. |
| | DCP-M | Tricyclodecane dimethanol dimethacrylate | Kyoei Kagaku Kogyo K.K. |
| | TMPTA | Trimethylolpropane triacrylate | Daicel-Allnex Ltd. |
| | EBECRYL135 | Trimethylolpropane propoxytriacrylate | Daicel-Allnex Ltd. |
| | TMPEOTA | Trimethylolpropane ethoxytriacrylate | Daicel-Allnex Ltd. |
| | TPGDA | Tripropylene glycol diacrylate | Daicel-Allnex Ltd. |
| | 1,6-HDDA | 1,6-Hexanediol diacrylate | Kyoei Kagaku Kogyo K.K. |
| | 1,9-NDDA | 1,9-Nonanediol diacrylate | Kyoei Kagaku Kogyo K.K. |
| | NP-A | Neopentyl glycol diacrylate | Kyoei Kagaku Kogyo K.K. |
| | 4EG-A | PEG 200 diacrylate | Kyoei Kagaku Kogyo K.K. |
| | 9EG-A | PEG 400 diacrylate | Kyoei Kagaku Kogyo K.K. |
| | 16EG-A | PEG 600 diacrylate | Kyoei Kagaku Kogyo K.K. |
| | MPD-A | 3-Methyl-1,5-pentanediol diacrylate | Kyoei Kagaku Kogyo K.K. |
| | EBECRYL8402 | Urethane acrylate, bifunctional | Daicel-Allnex Ltd. |
| | EBECRYL4858 | Urethane acrylate, bifunctional | Daicel-Allnex Ltd. |
| | EBECRYL180 | Pentaerythritol tetraacrylate | Daicel-Allnex Ltd. |

TABLE 1-continued

|  | Product No. | | Manufacturer |
|---|---|---|---|
| Component (A2), monofunctional | IBOA | Isobornyl acrylate | Daicel-Allnex Ltd. |
|  | FA-513AS | Tricyclodecane acrylate | Hitachi Chemical Co., Ltd. |
|  | FA-511AS | Dicyclopentenyl acrylate | Hitachi Chemical Co., Ltd. |
|  | 2HEA | 2-Hydroxyethyl acrylate | Wako Pure Chemical Industries Ltd. |
|  | ODA-L | Octyl/decyl acrylate | Daicel-Allnex Ltd. |
| Component (B) | Irgacure 907 | α-Aminoalkylphenone-type photo-radical polymerization initiator | BASF Japan Ltd. |
|  | Irgacure 369 | α-Aminoalkylphenone-type photo-radical polymerization initiator | BASF Japan Ltd. |
|  | Irgacure 379EG | α-Aminoalkylphenone-type photo-radical polymerization initiator | BASF Japan Ltd. |
|  | TPO | Acylphosphine oxide-type photo-radical polymerization initiator | BASF Japan Ltd. |
| Component (C) | YD-127 | Bisphenol A- type epoxy resin | Nippon Steel & Sumitomo Metal Corporation |
|  | YDF-170 | Bisphenol F-type epoxy resin | Nippon Steel & Sumitomo Metal Corporation |
|  | EX-211 | Neopentyl glycol diglycidyl ether | Nagase ChemteX Corporation |
|  | JER630 | Glycidylamine-type epoxy resin | Mitsubishi Chemical Corporation |
|  | JER152 | Phenol novolac-type epoxy resin | Mitsubishi Chemical Corporation |
|  | TETRAD-X | Glycidylamine-type epoxy resin | Mitsubishi Gas Chemical Company, Inc. |
|  | TETRAD-C | Glycidylamine-type epoxy resin | Mitsubishi Gas Chemical Company, Inc. |
| Component (D) | EH105L | Dimethylthiotoluenediamine | ADEKA |
|  | DETDA | Diethyltoluenediamine | Mitsui Fine Chemicals, Inc. |
|  | Curehard MED | Diaminodiethyldimethyldiphenylmethane | Ihara Chemical Industry Co., Ltd. |
|  | EPON HPT 1062 | α,α'-Bis(4-aminophenyl)-p-diisopropylbenzene | Shell Chemicals Japan Ltd. |
|  | DDS | Diaminodiphenylsulfone | Wakayama Seika Kogyo Co., Ltd. |
|  | DDM | Diaminodiphenylmethane | Sumitomo Chemical Co., Ltd. |
|  | 4,4'-DADPE | 4,4'-Diaminodiphenylether | Mitsui Fine Chemicals, Inc. |
|  | m-PDA | Methaphenylenediamine | Mitsui Chemicals, Inc. |
|  | m/p-APA | α-(m/p-Aminophenyl)ethylamine | Mitsui Chemicals, Inc. |
|  | MXDA | m-Xylenediamine | Mitsubishi Gas Chemical Company, Inc. |
| Another thermal curing agent | MDA | Menthenediamine | Dow Chemical Company |
|  | IPDA | Isophoronediamine | Tokyo Chemical Industry Co., Ltd. |
|  | Laromin C-260 | Bis(4-amino-3-methyldicyclohexyl)methane | BASF Japan Ltd. |
|  | WONDAMINE HM | Diaminodicyclohexylmethane | New Japan Chemical Co., Ltd. |
|  | 13BAC | Bis(aminomethyl)cyclohexane | Mitsubishi Gas Chemical Company, Inc. |
|  | N-AEP | N-Aminoethylpiperazine | Koei Chemical Co., Ltd. |
|  | EPOMATE B-002 | 3,9-Bis(3aminopropyl)2,4,8,10-tetraoxaspiro(5,5)undecane | Mitsubishi Chemical Corporation |

TABLE 2

|  | Product No. | Manufacturer |
|---|---|---|
| Component (E) | Pyrazole | Tokyo Chemical Industry Co., Ltd. |
|  | 3-Amino-5-tert-butylpyrazole | Tokyo Chemical Industry Co., Ltd. |
|  | 1-Allyl-3,5-dimethylpyrazole | Tokyo Chemical Industry Co., Ltd. |
|  | 3-Aminopyrazole | Tokyo Chemical Industry Co., Ltd. |
|  | 3,5-Dimethylpyrazole | Otsuka Chemical Co., Ltd. |
|  | 1,2,4-Triazole | Otsuka Chemical Co., Ltd. |
|  | 4-Amino-1,2,4-triazole | Otsuka Chemical Co., Ltd. |
|  | 1,2,3-triazole | Otsuka Chemical Co., Ltd. |
|  | 3-Mercapto-1,2,4-triazole | Otsuka Chemical Co., Ltd. |
|  | 1-[N,N-Bis(2-ethylhexyl)aminomethyl]benzotriazole | Tokyo Chemical Industry Co., Ltd. |
|  | 1-[N,N-Bis(2-ethylhexyl)aminomethyl]methylbenzotriazole | Tokyo Chemical Industry Co., Ltd. |
|  | 2,2'-[[(Methyl-1H-benzotriazole-1-yl)methyl]imino]bisethanol | Tokyo Chemical Industry Co., Ltd. |
|  | Benzimidazole | Wako |
|  | 1-Methylbenzimidazole | Wako |

TABLE 2-continued

| | Product No. | | Manufacturer |
|---|---|---|---|
| | 1,2-Dimethylimidazole | | Shikoku Chemicals Corporation |
| | 1-Benzyl-2-methylimidazole | | Shikoku Chemicals Corporation |
| | 1-Benzyl-2-phenylimidazole | | Shikoku Chemicals Corporation |
| | 1-Cyanoethyl-2-methylimidazole | | Shikoku Chemicals Corporation |
| | 1-Cyanoethyl-2-ethyl-4-methylimidazole | | Shikoku Chemicals Corporation |
| Solvent (F) | Propylene glycol 1-monomethyl ether 2-acetate | | Tokyo Chemical Industry Co., Ltd. |
| | Dipropylene glycol monomethyl ether | | Tokyo Chemical Industry Co., Ltd. |
| | Dipropylene glycol dimethyl ether | | Tokyo Chemical Industry Co., Ltd. |
| Color material (G) | 650M | Phthalocyanine-based compound | Orient Chemical Industries Co., Ltd. |
| | NUBIAN BLUE PS-5630 | Anthraquinone-based compound | Orient Chemical Industries Co., Ltd. |
| | valifast black 3804 | Azo-based compound | Orient Chemical Industries Co., Ltd. |
| | valifast black 1821 | Nigrosine-based compound | Orient Chemical Industries Co., Ltd. |

TABLE 3

| | | Product No. | Example 1 | Example 2 | Example 3 | Example 4 | Example 5 |
|---|---|---|---|---|---|---|---|
| Components to be added (part by weight) | Component (A1), bifunctional or higher | IRR214-K | 70 | 70 | 70 | 70 | 70 |
| | | DCP-M | | | | | |
| | | TMPTA | | | | | |
| | | EBECRYL135 | | | | | |
| | | TMPEOTA | | | | | |
| | | TPGDA | | | | | |
| | | 1,6-HDDA | | | | | |
| | | 1,9-NDDA | | | | | |
| | | NP-A | | | | | |
| | | 4EG-A | | | | | |
| | | 9EG-A | | | | | |
| | | 16EG-A | | | | | |
| | | MPD-A | | | | | |
| | | EBECRYL8402 | | | | | |
| | | EBECRYL4858 | | | | | |
| | | EBECRYL180 | | | | | |
| | Component (B) | Irgacure 907 | 5 | 5 | 5 | 5 | 5 |
| | | Irgacure 369 | | | | | |
| | | Irgacure 379EG | | | | | |
| | | TPO | | | | | |
| | Component (C) | YD-127 | 15 | 15 | 15 | 15 | 15 |
| | | YDF-170 | | | | | |
| | | EX-211 | | | | | |
| | | JER630 | | | | | |
| | | JER152 | | | | | |
| | | TETRAD-X | | | | | |
| | | TETRAD-C | | | | | |
| | Component (D) | EH105L | 10 | | | | |
| | | DETDA | | 10 | | | |
| | | Curehard MED | | | 10 | | |
| | | EPON HPT 1062 | | | | 10 | |
| | | DDS | | | | | 10 |
| | | DDM | | | | | |
| | | 4,4'-DADPE | | | | | |
| | | m-PDA | | | | | |
| | | m/p-APA | | | | | |
| | | MXDA | | | | | |
| Evaluation | | (1) Viscosity | D | D | D | D | D |
| | | (2) Increase in viscosity | ⊙ | ⊙ | ⊙ | ⊙ | ⊙ |
| | | (3) Inkjet dischargeability | ⊙ | ⊙ | ○ | ⊙ | ⊙ |
| | | (4) Wettability/spreadability | ⊙ | ⊙ | ⊙ | ⊙ | ⊙ |
| | | (5) Length of pot life | ⊙ | ⊙ | ⊙ | ⊙ | ⊙ |
| | | (6) Heat resistance | ○ | ○ | ○ | ○ | ○ |
| | | (7) Acid resistance | Δ | Δ | Δ | Δ | Δ |

TABLE 3-continued

|  |  |  | | | | | |
|---|---|---|---|---|---|---|---|
| | | (8) Insulation reliability (migration resistance) | ○ | ○ | ○ | ○ | ○ |
| | | (9) Long-term reliability (cooling/heating cycle resistance evaluation) [500 cycles] | ○ | ○ | ○ | ○ | ○ |
| | | (9) Long-term reliability (cooling/heating cycle resistance evaluation) [1000 cycles] | ○ | ○ | ○ | Δ | Δ |

| | | Product No. | Example 6 | Example 7 | Example 8 | Example 9 | Example 10 |
|---|---|---|---|---|---|---|---|
| Components to be added (part by weight) | Component (A1), bifunctional or higher | IRR214-K | 70 | 70 | 70 | 70 | 70 |
| | | DCP-M | | | | | |
| | | TMPTA | | | | | |
| | | EBECRYL135 | | | | | |
| | | TMPEOTA | | | | | |
| | | TPGDA | | | | | |
| | | 1,6-HDDA | | | | | |
| | | 1,9-NDDA | | | | | |
| | | NP-A | | | | | |
| | | 4EG-A | | | | | |
| | | 9EG-A | | | | | |
| | | 16EG-A | | | | | |
| | | MPD-A | | | | | |
| | | EBECRYL8402 | | | | | |
| | | EBECRYL4858 | | | | | |
| | | EBECRYL180 | | | | | |
| | Component (B) | Irgacure 907 | 5 | 5 | 5 | 5 | 5 |
| | | Irgacure 369 | | | | | |
| | | Irgacure 379EG | | | | | |
| | | TPO | | | | | |
| | Component (C) | YD-127 | 15 | 15 | 15 | 15 | 15 |
| | | YDF-170 | | | | | |
| | | EX-211 | | | | | |
| | | JER630 | | | | | |
| | | JER152 | | | | | |
| | | TETRAD-X | | | | | |
| | | TETRAD-C | | | | | |
| | Component (D) | EH105L | | | | | |
| | | DETDA | | | | | |
| | | Curehard MED | | | | | |
| | | EPON HPT 1062 | | | | | |
| | | DDS | | | | | |
| | | DDM | 10 | | | | |
| | | 4,4'-DADPE | | 10 | | | |
| | | m-PDA | | | 10 | | |
| | | m/p-APA | | | | 10 | |
| | | MXDA | | | | | 10 |
| Evaluation | | (1) Viscosity | D | D | D | D | D |
| | | (2) Increase in viscosity | ○○ | ○○ | ○○ | ○○ | ○○ |
| | | (3) Inkjet dischargeability | ○ | ○○ | ○○ | ○○ | ○○ |
| | | (4) Wettability/spreadability | ○○ | ○○ | ○○ | ○○ | ○○ |
| | | (5) Length of pot life | ○○ | ○○ | ○○ | ○○ | ○○ |
| | | (6) Heat resistance | ○ | ○ | ○ | ○ | ○ |
| | | (7) Acid resistance | Δ | Δ | Δ | Δ | Δ |
| | | (8) Insulation reliability (migration resistance) | ○ | ○ | ○ | ○ | ○ |
| | | (9) Long-term reliability (cooling/heating cycle resistance evaluation) [500 cycles] | ○ | ○ | ○ | ○ | ○ |
| | | (9) Long-term reliability (cooling/heating cycle resistance evaluation) [1000 cycles] | ○ | Δ | Δ | Δ | Δ |

TABLE 4

|  |  | Product No. | Example 11 | Example 12 | Example 13 | Example 14 | Example 15 | Example 16 | Example 17 | Example 18 | Example 19 |
|---|---|---|---|---|---|---|---|---|---|---|---|
| Components to be added (part by weight) | Component (A1), bifunctional or higher | IFRR214-K | 70 | 70 | 70 | 70 | 70 | 70 | 70 | 70 | 70 |
|  |  | DCP-M |  |  |  |  |  |  |  |  |  |
|  |  | TMPTA |  |  |  |  |  |  |  |  |  |
|  |  | EBECRYL135 |  |  |  |  |  |  |  |  |  |
|  |  | TMPEOTA |  |  |  |  |  |  |  |  |  |
|  |  | TPGDA |  |  |  |  |  |  |  |  |  |
|  |  | 1,6-HDDA |  |  |  |  |  |  |  |  |  |
|  |  | 1,9-NDDA |  |  |  |  |  |  |  |  |  |
|  |  | NP-A |  |  |  |  |  |  |  |  |  |
|  |  | 4EG-A |  |  |  |  |  |  |  |  |  |
|  |  | 9EG-A |  |  |  |  |  |  |  |  |  |
|  |  | 16EG-A |  |  |  |  |  |  |  |  |  |
|  |  | MPD-A |  |  |  |  |  |  |  |  |  |
|  |  | EBECRYL8402 |  |  |  |  |  |  |  |  |  |
|  |  | EBECRYL4858 |  |  |  |  |  |  |  |  |  |
|  |  | EBECRYL180 |  |  |  |  |  |  |  |  |  |
|  | Component (B) | Irgacure 907 |  |  |  | 5 | 5 | 5 | 5 | 5 | 5 |
|  |  | Irgacure 369 | 5 |  |  |  |  |  |  |  |  |
|  |  | Irgacure 379EG |  | 5 |  |  |  |  |  |  |  |
|  |  | TPO |  |  | 5 |  |  |  |  |  |  |
|  | Component (C) | YD-127 | 15 | 15 | 15 |  |  |  |  |  |  |
|  |  | YDF-170 |  |  |  | 15 |  |  |  |  |  |
|  |  | EX-211 |  |  |  |  | 15 |  |  |  |  |
|  |  | JER630 |  |  |  |  |  | 15 |  |  |  |
|  |  | JER152 |  |  |  |  |  |  | 15 |  |  |
|  |  | TETRAD-X |  |  |  |  |  |  |  | 15 |  |
|  |  | TETRAD-C |  |  |  |  |  |  |  |  | 15 |
|  | Component (D) | EH105L | 10 | 10 | 10 | 10 | 10 | 10 | 10 | 10 | 10 |
|  |  | DETDA |  |  |  |  |  |  |  |  |  |
|  |  | Curehard MED |  |  |  |  |  |  |  |  |  |
|  |  | EPON HPT 1062 |  |  |  |  |  |  |  |  |  |
|  |  | DDS |  |  |  |  |  |  |  |  |  |
|  |  | DDM |  |  |  |  |  |  |  |  |  |
|  |  | 4,4'-DADPE |  |  |  |  |  |  |  |  |  |
|  |  | m-PDA |  |  |  |  |  |  |  |  |  |
|  |  | m/p-APA |  |  |  |  |  |  |  |  |  |
|  |  | MXDA |  |  |  |  |  |  |  |  |  |
| Evaluation | (1) Viscosity |  | D | D | D | D | D | D | D | D | D |
|  | (2) Increase in viscosity |  | ○○ | ○○ | ○○ | ○○ | ○○ | ○○ | ○○ | ○○ | ○○ |
|  | (3) Inkjet dischargeability |  | ○○ | ○○ | ○○ | ○○ | ○○ | ○○ | ○○ | ○○ | ○○ |
|  | (4) Wettability/spreadability |  | ○○ | ○○ | ○○ | ○○ | ○○ | ○○ | ○○ | ○○ | ○○ |
|  | (5) Length of pot life |  | ○○ | ○○ | ○○ | ○○ | ○○ | ○○ | ○○ | ○○ | ○○ |
|  | (6) Heat resistance |  | ○ | ○ | ○ | ○ | ○ | ○ | ○ | ○ | ○ |
|  | (7) Acid resistance |  | Δ | Δ | Δ | Δ | Δ | Δ | Δ | Δ | Δ |
|  | (8) Insulation reliability (migration resistance) |  | ○ | ○ | ○ | ○ | ○ | ○ | ○ | ○ | ○ |
|  | (9) Long-term reliability (cooling/heating cycle resistance evaluation) [500 cycles] |  | ○ | ○ | ○ | ○ | ○ | ○ | ○ | ○ | ○ |
|  | (9) Long-term reliability (cooling/heating cycle resistance evaluation) [1000 cycles] |  | ○ | ○ | ○ | ○ | ○ | ○ | ○ | ○ | ○ |

TABLE 5

|  |  | Product No. | Example 20 | Example 21 | Example 22 | Example 23 | Example 24 | Example 25 | Example 26 | Example 27 | Example 28 | Example 29 |
|---|---|---|---|---|---|---|---|---|---|---|---|---|
| Components to be added (part by weight) | Component (A1), bifunctional or higher | IRR214-K |  |  |  |  |  |  |  |  |  |  |
|  |  | DCP-M | 70 |  |  |  |  |  |  |  |  |  |
|  |  | TMPTA |  | 70 |  |  |  |  |  |  |  |  |
|  |  | EBECRYL135 |  |  | 70 |  |  |  |  |  |  |  |
|  |  | TMPEOTA |  |  |  | 70 |  |  |  |  |  |  |
|  |  | TPGDA |  |  |  |  | 70 |  |  |  |  |  |
|  |  | 1,6-HDDA |  |  |  |  |  | 70 |  |  |  |  |
|  |  | 1,9-NDDA |  |  |  |  |  |  | 70 |  |  |  |
|  |  | NP-A |  |  |  |  |  |  |  | 70 |  |  |
|  |  | 4EG-A |  |  |  |  |  |  |  |  | 70 |  |
|  |  | 9EG-A |  |  |  |  |  |  |  |  |  | 70 |

TABLE 5-continued

|  |  | Product No. | Example 20 | Example 21 | Example 22 | Example 23 | Example 24 | Example 25 | Example 26 | Example 27 | Example 28 | Example 29 |
|---|---|---|---|---|---|---|---|---|---|---|---|---|
|  |  | 16EG-A |  |  |  |  |  |  |  |  |  |  |
|  |  | MPD-A |  |  |  |  |  |  |  |  |  |  |
|  |  | EBECRYL8402 |  |  |  |  |  |  |  |  |  |  |
|  |  | EBECRYL4858 |  |  |  |  |  |  |  |  |  |  |
|  |  | EBECRYL180 |  |  |  |  |  |  |  |  |  |  |
|  | Component (B) | Irgacure 907 | 5 | 5 | 5 | 5 | 5 | 5 | 5 | 5 | 5 | 5 |
|  |  | Irgacure 369 |  |  |  |  |  |  |  |  |  |  |
|  |  | Irgacure 379EG |  |  |  |  |  |  |  |  |  |  |
|  |  | TPO |  |  |  |  |  |  |  |  |  |  |
|  | Component (C) | YD-127 | 15 | 15 | 15 | 15 | 15 | 15 | 15 | 15 | 15 | 15 |
|  |  | YDF-170 |  |  |  |  |  |  |  |  |  |  |
|  |  | EX-211 |  |  |  |  |  |  |  |  |  |  |
|  |  | JER630 |  |  |  |  |  |  |  |  |  |  |
|  |  | JER152 |  |  |  |  |  |  |  |  |  |  |
|  |  | TETRAD-X |  |  |  |  |  |  |  |  |  |  |
|  |  | TETRAD-C |  |  |  |  |  |  |  |  |  |  |
|  | Component (D) | EH105L | 10 | 10 | 10 | 10 | 10 | 10 | 10 | 10 | 10 | 10 |
|  |  | DETDA |  |  |  |  |  |  |  |  |  |  |
|  |  | Curehard MED |  |  |  |  |  |  |  |  |  |  |
|  |  | EPON HPT 1062 |  |  |  |  |  |  |  |  |  |  |
|  |  | DDS |  |  |  |  |  |  |  |  |  |  |
|  |  | DDM |  |  |  |  |  |  |  |  |  |  |
|  |  | 4,4'-DADPE |  |  |  |  |  |  |  |  |  |  |
|  |  | m-PDA |  |  |  |  |  |  |  |  |  |  |
|  |  | m/p-APA |  |  |  |  |  |  |  |  |  |  |
|  |  | MXDA |  |  |  |  |  |  |  |  |  |  |
| Evaluation | (1) Viscosity |  | D | D | D | D | D | D | D | D | D | D |
|  | (2) Increase in viscosity |  | ○○ | ○○ | ○○ | ○○ | ○○ | ○○ | ○○ | ○○ | ○○ | ○○ |
|  | (3) Inkjet dischargeability |  | ○○ | ○○ | ○○ | ○○ | ○○ | ○○ | ○○ | ○○ | ○○ | ○○ |
|  | (4) Wettability/spreadability |  | ○○ | ○○ | ○○ | ○○ | ○○ | ○○ | ○○ | ○○ | ○○ | ○○ |
|  | (5) Length of pot life |  | ○○ | ○○ | ○○ | ○○ | ○○ | ○○ | ○○ | ○○ | ○○ | ○○ |
|  | (6) Heat resistance |  | ○ | ○ | ○ | ○ | ○ | ○ | ○ | ○ | ○ | ○ |
|  | (7) Acid resistance |  | Δ | Δ | Δ | Δ | Δ | Δ | Δ | Δ | Δ | Δ |
|  | (8) Insulation reliability (migration resistance) |  | ○ | ○ | ○ | ○ | ○ | ○ | ○ | ○ | ○ | ○ |
|  | (9) Long-term reliability (cooling/heating cycle resistance evaluation) [500 cycles] |  | ○ | ○ | ○ | ○ | ○ | ○ | ○ | ○ | ○ | ○ |
|  | (9) Long-term reliability (cooling/heating cycle resistance evaluation) [1000 cycles] |  | ○ | ○ | ○ | ○ | ○ | ○ | ○ | ○ | ○ | ○ |

TABLE 6

|  |  | Product No. | Example 30 | Example 31 | Example 32 | Example 33 | Example 34 | Example 35 | Example 36 | Example 37 | Example 38 | Example 39 |
|---|---|---|---|---|---|---|---|---|---|---|---|---|
| Components to be added (part by weight) | Component (A1), bifunctional or higher | IRR214-K |  |  |  |  |  | 60 | 60 | 60 | 60 | 60 |
|  |  | DCP-M |  |  |  |  |  |  |  |  |  |  |
|  |  | TMPTA |  |  |  |  |  |  |  |  |  |  |
|  |  | EBECRYL135 |  |  |  |  |  |  |  |  |  |  |
|  |  | TMPEOTA |  |  |  |  |  |  |  |  |  |  |
|  |  | TPGDA |  |  |  |  |  |  |  |  |  |  |
|  |  | 1,6-HDDA |  |  |  |  |  |  |  |  |  |  |
|  |  | 1,9-NDDA |  |  |  |  |  |  |  |  |  |  |
|  |  | NP-A |  |  |  |  |  |  |  |  |  |  |
|  |  | 4EG-A |  |  |  |  |  |  |  |  |  |  |
|  |  | 9EG-A |  |  |  |  |  |  |  |  |  |  |
|  |  | 16EG-A | 70 |  |  |  |  |  |  |  |  |  |
|  |  | MPD-A |  | 70 |  |  |  |  |  |  |  |  |
|  |  | EBECRYL8402 |  |  | 70 |  |  |  |  |  |  |  |
|  |  | EBECRYL4858 |  |  |  | 70 |  |  |  |  |  |  |
|  |  | EBECRYL180 |  |  |  |  | 70 |  |  |  |  |  |

TABLE 6-continued

| | Product No. | Example 30 | Example 31 | Example 32 | Example 33 | Example 34 | Example 35 | Example 36 | Example 37 | Example 38 | Example 39 |
|---|---|---|---|---|---|---|---|---|---|---|---|
| Component (A2), monofunctional | IBOA | | | | | | 10 | | | | |
| | FA-513AS | | | | | | | 10 | | | |
| | FA-511AS | | | | | | | | 10 | | |
| | 2HEA | | | | | | | | | 10 | |
| | ODA-L | | | | | | | | | | 10 |
| Component (B) | Irgacure 907 | 5 | 5 | 5 | 5 | 5 | 5 | 5 | 5 | 5 | 5 |
| | Irgacure 369 | | | | | | | | | | |
| | Irgacure 379EG | | | | | | | | | | |
| | TPO | | | | | | | | | | |
| Component (C) | YD-127 | 15 | 15 | 15 | 15 | 15 | 15 | 15 | 15 | 15 | 15 |
| | YDF-170 | | | | | | | | | | |
| | EX-211 | | | | | | | | | | |
| | JER630 | | | | | | | | | | |
| | JER152 | | | | | | | | | | |
| | TETRAD-X | | | | | | | | | | |
| | TETRAD-C | | | | | | | | | | |
| Component (D) | EH105L | 10 | 10 | 10 | 10 | 10 | 10 | 10 | 10 | 10 | 10 |
| | DETDA | | | | | | | | | | |
| | Curehard MED | | | | | | | | | | |
| | EPON HPT 1062 | | | | | | | | | | |
| | DDS | | | | | | | | | | |
| | DDM | | | | | | | | | | |
| | 4,4'-DADPE | | | | | | | | | | |
| | m-PDA | | | | | | | | | | |
| | m/p-APA | | | | | | | | | | |
| | MXDA | | | | | | | | | | |
| Evaluation (1) Viscosity | | D | D | D | D | D | D | D | D | D | D |
| (2) Increase in viscosity | | ○○ | ○○ | ○○ | ○○ | ○○ | ○○ | ○○ | ○○ | ○○ | ○○ |
| (3) Inkjet dischargeability | | ○○ | ○○ | ○○ | ○○ | ○○ | ○○ | ○○ | ○○ | ○○ | ○○ |
| (4) Wettability/spreadability | | ○○ | ○○ | ○○ | ○○ | ○○ | ○○ | ○○ | ○○ | ○○ | ○○ |
| (5) Length of pot life | | ○○ | ○○ | ○○ | ○○ | ○○ | ○○ | ○○ | ○○ | ○○ | ○○ |
| (6) Heat resistance | | ○ | ○ | ○ | ○ | ○ | ○ | ○ | ○ | ○ | ○ |
| (7) Acid resistance | | Δ | Δ | Δ | Δ | Δ | Δ | Δ | Δ | Δ | Δ |
| (8) Insulation reliability (migration resistance) | | ○ | ○ | ○ | ○ | ○ | ○ | ○ | ○ | ○ | ○ |
| (9) Long-term reliability (cooling/heating cycle resistance evaluation) [500 cycles] | | ○ | ○ | ○ | ○ | ○ | ○ | ○ | ○ | ○ | ○ |
| (9) Long-term reliability (cooling/heating cycle resistance evaluation) [1000 cycles] | | ○ | ○ | ○ | ○ | ○ | ○ | ○ | ○ | ○ | ○ |

TABLE 7

| | | Product No. | Example 40 | Example 41 | Example 42 | Example 43 | Example 44 | Example 45 |
|---|---|---|---|---|---|---|---|---|
| Components to be added (part by weight) | Component (A1), bifunctional or higher | IRR214-K | 60 | 45 | 69 | 69 | 69 | 69 |
| | | DCP-M | | | | | | |
| | | TMPTA | | | | | | |
| | | EBECRYL135 | | | | | | |
| | | TMPEOTA | | | | | | |
| | | TPGDA | | | | | | |
| | | 1,6-HDDA | | | | | | |
| | | 1,9-NDDA | | | | | | |
| | | NP-A | | | | | | |
| | | 4EG-A | | | | | | |
| | | 9EG-A | | | | | | |
| | | 16EG-A | | | | | | |
| | | MPD-A | | | | | | |
| | | EBECRYL8402 | | | | | | |
| | | EBECRYL4858 | | | | | | |
| | | EBECRYL180 | | | | | | |
| | Component (B) | Irgacure 907 | 5 | 5 | 5 | 5 | 5 | 5 |
| | | Irgacure 369 | | | | | | |
| | | Irgacure 379EG | | | | | | |
| | | TPO | | | | | | |

TABLE 7-continued

|  |  | Product No. | Example 40 | Example 41 | Example 42 | Example 43 | Example 44 | Example 45 |
|---|---|---|---|---|---|---|---|---|
|  | Component (C) | YD-127 | 20 | 30 | 15 | 15 | 15 | 15 |
|  |  | YDF-170 |  |  |  |  |  |  |
|  |  | EX-211 |  |  |  |  |  |  |
|  |  | JER630 |  |  |  |  |  |  |
|  |  | JER152 |  |  |  |  |  |  |
|  |  | TETRAD-X |  |  |  |  |  |  |
|  |  | TETRAD-C |  |  |  |  |  |  |
|  | Component (D) | EH105L | 15 | 20 | 10 | 10 | 10 | 10 |
|  |  | DETDA |  |  |  |  |  |  |
|  |  | Curehard MED |  |  |  |  |  |  |
|  |  | EPON HPT 1062 |  |  |  |  |  |  |
|  |  | DDS |  |  |  |  |  |  |
|  |  | DDM |  |  |  |  |  |  |
|  |  | 4,4'-DADPE |  |  |  |  |  |  |
|  |  | m-PDA |  |  |  |  |  |  |
|  |  | m/p-APA |  |  |  |  |  |  |
|  |  | MXDA |  |  |  |  |  |  |
|  | Color material (G) | 650M |  |  | 1 |  |  |  |
|  |  | NUBIAN BLUE PS-5630 |  |  |  | 1 |  |  |
|  |  | valifast black 3804 |  |  |  |  | 1 |  |
|  |  | valifast black 1821 |  |  |  |  |  | 1 |
| Evaluation |  | (1) Viscosity | D | C | D | D | D | D |
|  |  | (2) Increase in viscosity | ○○ | ○ | ○○ | ○○ | ○ | ○○ |
|  |  | (3) Inkjet dischargeability | ○○ | ○ | ○○ | ○○ | ○ | ○○ |
|  |  | (4) Wettability/spreadability | ○○ | ○ | ○○ | ○○ | ○ | ○○ |
|  |  | (5) Length of pot life | ○○ | ○ | ○○ | ○○ | ○ | ○○ |
|  |  | (6) Heat resistance | ○ | ○ | ○ | ○ | ○ | ○ |
|  |  | (7) Acid resistance | Δ | Δ | Δ | Δ | Δ | Δ |
|  |  | (8) Insulation reliability (migration resistance) | ○ | ○ | ○ | ○ | ○ | ○ |
|  |  | (9) Long-term reliability (cooling/heating cycle resistance evaluation) [500 cycles] | ○ | ○ | ○ | ○ | ○ | ○ |
|  |  | (9) Long-term reliability (cooling/heating cycle resistance evaluation) [1000 cycles] | ○ | ○ | ○ | ○ | Δ | ○ |

TABLE 8

|  |  | Product No. | Example 46 | Example 47 | Example 48 | Example 49 | Example 50 |
|---|---|---|---|---|---|---|---|
| Components to be added (part by weight) | Component (A1), bifunctional or higher | IFIR214-K | 70 | 70 | 70 | 70 | 70 |
|  |  | DCP-M |  |  |  |  |  |
|  |  | TMPTA |  |  |  |  |  |
|  |  | EBECRYL135 |  |  |  |  |  |
|  |  | TMPEOTA |  |  |  |  |  |
|  |  | TPGDA |  |  |  |  |  |
|  |  | 1,6-HDDA |  |  |  |  |  |
|  |  | 1,9-NDDA |  |  |  |  |  |
|  |  | NP-A |  |  |  |  |  |
|  |  | 4EG-A |  |  |  |  |  |
|  |  | 9EG-A |  |  |  |  |  |
|  |  | 16EG-A |  |  |  |  |  |
|  |  | MPD-A |  |  |  |  |  |
|  |  | EBECRYL8402 |  |  |  |  |  |
|  |  | EBECRYL4858 |  |  |  |  |  |
|  |  | EBECRYL180 |  |  |  |  |  |
|  | Component (B) | Irgacure 907 | 5 | 5 | 5 | 5 | 5 |
|  |  | Irgacure 369 |  |  |  |  |  |
|  |  | Irgacure 379EG |  |  |  |  |  |
|  |  | TPO |  |  |  |  |  |
|  | Component (C) | YD-127 | 15 | 15 | 15 | 15 | 15 |
|  |  | YDF-170 |  |  |  |  |  |
|  |  | EX-211 |  |  |  |  |  |
|  |  | JER630 |  |  |  |  |  |
|  |  | JER152 |  |  |  |  |  |
|  |  | TETRAD-X |  |  |  |  |  |
|  |  | TETRAD-C |  |  |  |  |  |
|  | Component (D) | EH105L |  |  |  |  |  |
|  |  | DETDA | 10 | 10 | 10 | 10 | 10 |
|  |  | Curehard MED |  |  |  |  |  |
|  |  | EPON HPT 1062 |  |  |  |  |  |
|  |  | DDS |  |  |  |  |  |

TABLE 8-continued

|  |  | Product No. | Example 46 | Example 47 | Example 48 | Example 49 | Example 50 |
|---|---|---|---|---|---|---|---|
|  |  | DDM |  |  |  |  |  |
|  |  | 4,4'-DADPE |  |  |  |  |  |
|  |  | m-PDA |  |  |  |  |  |
|  |  | m/p-APA |  |  |  |  |  |
|  |  | MXDA |  |  |  |  |  |
|  | Component (E) | Pyrazole | 0.5 |  |  |  |  |
|  |  | 3-Amino-5-tert-butylpyrazole |  | 0.5 |  |  |  |
|  |  | 1-Allyl-3,5-dimethylpyrazole |  |  | 0.5 |  |  |
|  |  | 3-Aminopyrazole |  |  |  | 0.5 |  |
|  |  | 3,5-Dimethylpyrazole |  |  |  |  | 0.5 |
|  |  | 1,2,4-Triazole |  |  |  |  |  |
|  |  | 4-Amino-1,2,4-triazole |  |  |  |  |  |
|  |  | 1,2,3-Triazole |  |  |  |  |  |
|  |  | 3-Mercapto-1,2,4-triazole |  |  |  |  |  |
|  |  | 1-[N,N-Bis(2-ethylhexyl)aminomethyl]benzotriazole |  |  |  |  |  |
|  |  | 1-[N,N-Bis(2-ethylhexyl)aminomethyl]methylbenzotriazole |  |  |  |  |  |
|  |  | 2,2'-[[(Methyl-1H-benzotriazole-1-yl)methyl]imino]bisethanol |  |  |  |  |  |
|  |  | Benzimidazole |  |  |  |  |  |
|  |  | 1-Methylbenzimidazole |  |  |  |  |  |
|  |  | 1,2-Dimethylimidazole |  |  |  |  |  |
|  |  | 1-Benzyl-2-methylimidazole |  |  |  |  |  |
|  |  | 1-Benzyl-2-phenylimidazole |  |  |  |  |  |
|  |  | 1-Cyanoethyl-2-methylimidazole |  |  |  |  |  |
|  |  | 1-Cyanoethyl-2-ethyl-4-methylimidazole |  |  |  |  |  |
| Evaluation | (1) Viscosity |  | D | D | D | D | D |
|  | (2) Increase in viscosity |  | ◯◯ | ◯◯ | ◯◯ | ◯◯ | ◯◯ |
|  | (3) Inkjet dischargeability |  | ◯◯ | ◯◯ | ◯ | ◯◯ | ◯◯ |
|  | (4) Wettability/spreadability |  | ◯◯ | ◯◯ | ◯◯ | ◯◯ | ◯◯ |
|  | (5) Length of pot life |  | ◯◯ | ◯◯ | ◯◯ | ◯◯ | ◯◯ |
|  | (6) Heat resistance |  | ◯ | ◯ | ◯ | ◯ | ◯ |
|  | (7) Acid resistance |  | ◯◯ | ◯◯ | ◯◯ | ◯◯ | ◯◯ |
|  | (8) Insulation reliability (migration resistance) |  | ◯ | ◯ | ◯ | ◯ | ◯ |
|  | (9) Long-term reliability (cooling/heating cycle resistance evaluation) [500 cycles] |  | ◯ | ◯ | ◯ | ◯ | ◯ |
|  | (9) Long-term reliability (cooling/heating cycle resistance evaluation) [1000 cycles] |  | ◯ | ◯ | ◯ | Δ | Δ |

TABLE 9

|  |  | Product No. | Example 51 | Example 52 | Example 53 | Example 54 | Example 55 |
|---|---|---|---|---|---|---|---|
| Components to be added (part by weight) | Component (A1), bifunctional or higher | IRR214-K | 70 | 70 | 70 | 70 | 70 |
|  |  | DCP-M |  |  |  |  |  |
|  |  | TMPTA |  |  |  |  |  |
|  |  | EBECRYL135 |  |  |  |  |  |
|  |  | TMPEOTA |  |  |  |  |  |
|  |  | TPGDA |  |  |  |  |  |
|  |  | 1,6-HDDA |  |  |  |  |  |
|  |  | 1,9-NDDA |  |  |  |  |  |
|  |  | NP-A |  |  |  |  |  |
|  |  | 4EG-A |  |  |  |  |  |
|  |  | 9EG-A |  |  |  |  |  |
|  |  | 16EG-A |  |  |  |  |  |
|  |  | MPD-A |  |  |  |  |  |
|  |  | EBECRYL8402 |  |  |  |  |  |
|  |  | EBECRYL4858 |  |  |  |  |  |
|  |  | EBECRYL180 |  |  |  |  |  |
|  | Component (B) | Irgacure 907 | 5 | 5 | 5 | 5 | 5 |
|  |  | Irgacure 369 |  |  |  |  |  |
|  |  | Irgacure 379EG |  |  |  |  |  |
|  |  | TPO |  |  |  |  |  |
|  | Component (C) | YD-127 | 15 | 15 | 15 | 15 | 15 |
|  |  | YDF-170 |  |  |  |  |  |
|  |  | EX-211 |  |  |  |  |  |
|  |  | JER630 |  |  |  |  |  |
|  |  | JER152 |  |  |  |  |  |
|  |  | TETRAD-X |  |  |  |  |  |
|  |  | TETRAD-C |  |  |  |  |  |
|  | Component (D) | EH105L |  |  |  |  |  |
|  |  | DETDA | 10 | 10 | 10 | 10 | 10 |
|  |  | Curehard MED |  |  |  |  |  |
|  |  | EPON HPT 1062 |  |  |  |  |  |
|  |  | DDS |  |  |  |  |  |

TABLE 9-continued

|  |  | Product No. | Example 51 | Example 52 | Example 53 | Example 54 | Example 55 |
|---|---|---|---|---|---|---|---|
|  |  | DDM |  |  |  |  |  |
|  |  | 4 4'-DADPE |  |  |  |  |  |
|  |  | m-PDA |  |  |  |  |  |
|  |  | m/p-APA |  |  |  |  |  |
|  |  | MXDA |  |  |  |  |  |
|  | Component (E) | Pyrazole |  |  |  |  |  |
|  |  | 3-Amino-5-tert-butylpyrazole |  |  |  |  |  |
|  |  | 1-Allyl-3,5-dimethylpyrazole |  |  |  |  |  |
|  |  | 3-Aminopyrazole |  |  |  |  |  |
|  |  | 3,5-Dimethylpyrazole |  |  |  |  |  |
|  |  | 1,2,4-Triazole | 0.5 |  |  |  |  |
|  |  | 4-Amino-1,2,4-triazole |  | 0.5 |  |  |  |
|  |  | 1,2,3-Triazole |  |  | 0.5 |  |  |
|  |  | 3-Mercapto-1,2,4-triazole |  |  |  | 0.5 |  |
|  |  | 1-[N,N-Bis(2-ethylhexyl)aminomethyl]benzotriazole |  |  |  |  | 0.5 |
|  |  | 1-[N,N-Bis(2-ethylhexyl)aminomethyl]methylbenzotriazole |  |  |  |  |  |
|  |  | 2,2'-[[(Methyl-1H-benzotriazole-1-yl)methyl]imino]bisethanol |  |  |  |  |  |
|  |  | Benzimidazole |  |  |  |  |  |
|  |  | 1-Methylbenzimidazole |  |  |  |  |  |
|  |  | 1,2-Dimethylimidazole |  |  |  |  |  |
|  |  | 1-Benzyl-2-methylimidazole |  |  |  |  |  |
|  |  | 1-Benzyl-2-phenylimidazole |  |  |  |  |  |
|  |  | 1-Cyanoethyl-2-methylimidazole |  |  |  |  |  |
|  |  | 1-Cyanoethyl-2-ethyl-4-methylimidazole |  |  |  |  |  |
| Evaluation | (1) Viscosity |  | D | D | D | D | D |
|  | (2) Increase in viscosity |  | ⊚ | ⊚ | ⊚ | ⊚ | ⊚ |
|  | (3) Inkjet dischargeability |  | ○ | ⊚ | ⊚ | ⊚ | ⊚ |
|  | (4) Wettability/spreadability |  | ⊚ | ⊚ | ⊚ | ⊚ | ⊚ |
|  | (5) Length of pot life |  | ⊚ | ⊚ | ⊚ | ⊚ | ⊚ |
|  | (6) Heat resistance |  | ○ | ○ | ○ | ○ | ○ |
|  | (7) Acid resistance |  | ⊚ | ⊚ | ⊚ | ⊚ | ⊚ |
|  | (8) Insulation reliability (migration resistance) |  | ○ | ○ | ○ | ○ | ○ |
|  | (9) Long-term reliability (cooling/heating cycle resistance evaluation) [500 cycles] |  | ○ | ○ | ○ | ○ | ○ |
|  | (9) Long-term reliability (cooling/heating cycle resistance evaluation) [1000 cycles] |  | ○ | Δ | Δ | Δ | Δ |

TABLE 10

|  |  | Product No. | Example 56 | Example 57 | Example 58 | Example 59 | Example 60 |
|---|---|---|---|---|---|---|---|
| Components to be added (part by weight) | Component (A1), bifunctional or higher | IRR214-K | 70 | 70 | 70 | 70 | 70 |
|  |  | DCP-M |  |  |  |  |  |
|  |  | TMPTA |  |  |  |  |  |
|  |  | EBECRYL135 |  |  |  |  |  |
|  |  | TMPEOTA |  |  |  |  |  |
|  |  | TPGDA |  |  |  |  |  |
|  |  | 1,6-HDDA |  |  |  |  |  |
|  |  | 1,9-NDDA |  |  |  |  |  |
|  |  | Np-A |  |  |  |  |  |
|  |  | 4EG-A |  |  |  |  |  |
|  |  | 9EG-A |  |  |  |  |  |
|  |  | 16EG-A |  |  |  |  |  |
|  |  | MPD-A |  |  |  |  |  |
|  |  | EBECRYL8402 |  |  |  |  |  |
|  |  | EBECRYL4858 |  |  |  |  |  |
|  |  | EBECRYL180 |  |  |  |  |  |
|  | Component (B) | Irgacure 907 | 5 | 5 | 5 | 5 | 5 |
|  |  | Irgacure 369 |  |  |  |  |  |
|  |  | Irgacure 379EG |  |  |  |  |  |
|  |  | TPO |  |  |  |  |  |
|  | Component (C) | YD-127 | 15 | 15 | 15 | 15 | 15 |
|  |  | YDF-170 |  |  |  |  |  |
|  |  | EX-211 |  |  |  |  |  |
|  |  | JER630 |  |  |  |  |  |
|  |  | JER152 |  |  |  |  |  |
|  |  | TETRAD-X |  |  |  |  |  |
|  |  | TETRAD-C |  |  |  |  |  |
|  | Component (D) | EH105L |  |  |  |  |  |
|  |  | DETDA | 10 | 10 | 10 | 10 | 10 |
|  |  | Curehard MED |  |  |  |  |  |
|  |  | EPON HPT1062 |  |  |  |  |  |
|  |  | DDS |  |  |  |  |  |

TABLE 10-continued

|  |  | Product No. | Example 56 | Example 57 | Example 58 | Example 59 | Example 60 |
|---|---|---|---|---|---|---|---|
|  |  | DDM |  |  |  |  |  |
|  |  | 4 4'-DADpE |  |  |  |  |  |
|  |  | m-PDA |  |  |  |  |  |
|  |  | m/p-APA |  |  |  |  |  |
|  |  | MXDA |  |  |  |  |  |
|  | Component (E) | Pyrazole |  |  |  |  |  |
|  |  | 3-Amino-5-tert-butylpyrazole |  |  |  |  |  |
|  |  | 1-Allyl-3,5-dimethylpyrazole |  |  |  |  |  |
|  |  | 3-Aminopyrazole |  |  |  |  |  |
|  |  | 3,5-Dimethylpyrazole |  |  |  |  |  |
|  |  | 1,2,4-Triazole |  |  |  |  |  |
|  |  | 4-Amino-1,2,4-triazole |  |  |  |  |  |
|  |  | 1,2,3-Triazole |  |  |  |  |  |
|  |  | 3-Mercapto-1,2,4-triazole |  |  |  |  |  |
|  |  | 1-[N,N-Bis(2-ethylhexyl)aminomethyl]benzotriazole |  |  |  |  |  |
|  |  | 1-[N,N-Bis(2-ethylhexyl)aminomethyl]methylbenzotriazole | 0.5 |  |  |  |  |
|  |  | 2,2'-[[(Methyl-1H-benzotriazole-1-yl)methyl]imino]bisethanol |  | 0.5 |  |  |  |
|  |  | Benzimidazole |  |  | 0.5 |  |  |
|  |  | 1-Methylbenzimidazole |  |  |  | 0.5 |  |
|  |  | 1,2-Dimethylimidazole |  |  |  |  | 0.5 |
|  |  | 1-Benzyl-2-methylimidazole |  |  |  |  |  |
|  |  | 1-Benzyl-2-phenylimidazole |  |  |  |  |  |
|  |  | 1-Cyanoethyl-2-methylimidazole |  |  |  |  |  |
|  |  | 1-Cyanoethyl-2-ethyl-4-methylimidazole |  |  |  |  |  |
| Evaluation | (1) Viscosity |  | D | D | D | D | D |
|  | (2) Increase in viscosity |  | ○○ | ○○ | ○○ | ○○ | ○○ |
|  | (3) Inkjet dischargeability |  | ○○ | ○○ | ○○ | ○○ | ○○ |
|  | (4) Wettability/spreadability |  | ○○ | ○○ | ○○ | ○○ | ○○ |
|  | (5) Length of pot life |  | ○○ | ○○ | ○○ | ○○ | ○○ |
|  | (6) Heat resistance |  | ○ | ○ | ○ | ○ | ○ |
|  | (7) Acid resistance |  | ○○ | ○○ | ○ | ○ | ○ |
|  | (8) Insulation reliability (migration resistance) |  | ○ | ○ | ○ | ○ | ○ |
|  | (9) Long-term reliability (cooling/heating cycle resistance evaluation) [500 cycles] |  | ○ | ○ | ○ | ○ | ○ |
|  | (9) Long-term reliability (cooling/heating cycle resistance evaluation) [1000 cycles] |  | Δ | Δ | Δ | Δ | Δ |

TABLE 11

|  |  | Product No. | Example 61 | Example 62 | Example 63 | Example 64 | Example 65 |
|---|---|---|---|---|---|---|---|
| Components to be added (part by weight) | Component (A1), bifunctional or higher | IRR214-K | 70 | 70 | 70 | 70 | 70 |
|  |  | DCP-M |  |  |  |  |  |
|  |  | TMpTA |  |  |  |  |  |
|  |  | EBECRYL135 |  |  |  |  |  |
|  |  | TMPEOTA |  |  |  |  |  |
|  |  | TPGDA |  |  |  |  |  |
|  |  | 1,6-HDDA |  |  |  |  |  |
|  |  | 1,9-NDDA |  |  |  |  |  |
|  |  | NP-A |  |  |  |  |  |
|  |  | 4EG-A |  |  |  |  |  |
|  |  | 9EG-A |  |  |  |  |  |
|  |  | 16EG-A |  |  |  |  |  |
|  |  | MPD-A |  |  |  |  |  |
|  |  | EBECRYL8402 |  |  |  |  |  |
|  |  | EBECRYL4858 |  |  |  |  |  |
|  |  | EBECRYL180 |  |  |  |  |  |
|  | Component (B) | Irgacure 907 | 5 | 5 | 5 | 5 | 5 |
|  |  | Irgacure 369 |  |  |  |  |  |
|  |  | Irgacure 379EG |  |  |  |  |  |
|  |  | TPO |  |  |  |  |  |
|  | Component (C) | YD-127 | 15 | 15 | 15 | 15 | 15 |
|  |  | YDF-170 |  |  |  |  |  |
|  |  | EX-211 |  |  |  |  |  |
|  |  | JER630 |  |  |  |  |  |
|  |  | JER152 |  |  |  |  |  |
|  |  | TETRAD-X |  |  |  |  |  |
|  |  | TETRAD-C |  |  |  |  |  |
|  | Component (D) | EH105L |  |  |  |  |  |
|  |  | DETDA | 10 | 10 | 10 | 10 |  |
|  |  | Curehard MED |  |  |  |  | 10 |
|  |  | EPON HPT 1062 |  |  |  |  |  |
|  |  | DDS |  |  |  |  |  |

TABLE 11-continued

|  |  | Product No. | Example 61 | Example 62 | Example 63 | Example 64 | Example 65 |
|---|---|---|---|---|---|---|---|
|  | Component (E) | DDM |  |  |  |  |  |
|  |  | 4,4'-DADPE |  |  |  |  |  |
|  |  | m-PDA |  |  |  |  |  |
|  |  | m/p-APA |  |  |  |  |  |
|  |  | MXDA |  |  |  |  |  |
|  |  | Pyrazole |  |  |  |  | 0.5 |
|  |  | 3-Amino-5-tert-butylpyrazole |  |  |  |  |  |
|  |  | 1-Allyl-3,5-dimethylpyrazole |  |  |  |  |  |
|  |  | 3-Aminopyrazole |  |  |  |  |  |
|  |  | 3,5-Dimethylpyrazole |  |  |  |  |  |
|  |  | 1,2,4-Triazole |  |  |  |  |  |
|  |  | 4-Amino-1,2,4-triazole |  |  |  |  |  |
|  |  | 1,2,3-Triazole |  |  |  |  |  |
|  |  | 3-Mercapto-1,2,4-triazole |  |  |  |  |  |
|  |  | 1-[N,N-Bis(2-ethylhexyl)aminomethyl]benzotriazole |  |  |  |  |  |
|  |  | 1-[N,N-Bis(2-ethylhexyl)aminomethyl]methylbenzotriazole |  |  |  |  |  |
|  |  | 2,2'-[[(Methyl-1H-benzotriazole-1-yl)methyl]imino]bisethanol |  |  |  |  |  |
|  |  | Benzimidazole |  |  |  |  |  |
|  |  | 1-Methylbenzimidazole |  |  |  |  |  |
|  |  | 1,2-Dimethylimidazole |  |  |  |  |  |
|  |  | 1-Benzyl-2-methylimidazole | 0.5 |  |  |  |  |
|  |  | 1-Benzyl-2-phenylimidazole |  | 0.5 |  |  |  |
|  |  | 1-Cyanoethyl-2-methylimidazole |  |  | 0.5 |  |  |
|  |  | 1-Cyanoethyl-2-ethyl-4-methylimidazole |  |  |  | 0.5 |  |
| Evaluation | (1) Viscosity |  | D | D | D | D | D |
|  | (2) Increase in viscosity |  | ○○ | ○○ | ○○ | ○○ | ○○ |
|  | (3) Inkjet dischargeability |  | ○○ | ○○ | ○○ | ○○ | ○○ |
|  | (4) Wettability/spreadability |  | ○○ | ○○ | ○○ | ○○ | ○○ |
|  | (5) Length of pot life |  | ○○ | ○○ | ○○ | ○○ | ○○ |
|  | (6) Heat resistance |  | ○ | ○ | ○ | ○ | ○ |
|  | (7) Acid resistance |  | ○ | ○ | ○ | ○ | ○○ |
|  | (8) Insulation reliability (migration resistance) |  | ○ | ○ | ○ | ○ | ○ |
|  | (9) Long-term reliability (cooling/heating cycle resistance evaluation) [500 cycles] |  | ○ | ○ | ○ | ○ | ○ |
|  | (9) Long-term reliability (cooling/heating cycle resistance evaluation) [1000 cycles] |  | Δ | Δ | Δ | Δ | ○ |

TABLE 12

|  |  | Product No. | Example 66 | Example 67 | Example 68 | Example 69 | Example 70 |
|---|---|---|---|---|---|---|---|
| Components to be added (part by weight) | Component (A1), bifunctional or higher | IRR214-K | 70 | 70 | 70 | 70 | 70 |
|  |  | DCP-M |  |  |  |  |  |
|  |  | TMPTA |  |  |  |  |  |
|  |  | EBECRYL135 |  |  |  |  |  |
|  |  | TMPEOTA |  |  |  |  |  |
|  |  | TPGDA |  |  |  |  |  |
|  |  | 1,6-HDDA |  |  |  |  |  |
|  |  | 1 9-NDDA |  |  |  |  |  |
|  |  | NP-A |  |  |  |  |  |
|  |  | 4EG-A |  |  |  |  |  |
|  |  | 9EG-A |  |  |  |  |  |
|  |  | 16EG-A |  |  |  |  |  |
|  |  | MPD-A |  |  |  |  |  |
|  |  | EBECRYL8402 |  |  |  |  |  |
|  |  | EBECRYL4858 |  |  |  |  |  |
|  |  | EBECRYL180 |  |  |  |  |  |
|  | Component (B) | Irgacure 907 | 5 | 5 | 5 | 5 | 5 |
|  |  | Irgacure 369 |  |  |  |  |  |
|  |  | Irgacure 379EG |  |  |  |  |  |
|  |  | TPO |  |  |  |  |  |
|  | Component (C) | YD-127 | 15 | 15 | 15 | 15 | 15 |
|  |  | YDF-170 |  |  |  |  |  |
|  |  | EX-211 |  |  |  |  |  |
|  |  | JER630 |  |  |  |  |  |
|  |  | JER152 |  |  |  |  |  |
|  |  | TETRAD-X |  |  |  |  |  |
|  |  | TETRAD-C |  |  |  |  |  |
|  | Component (D) | EH105L |  |  |  |  |  |
|  |  | DETDA |  |  |  |  |  |
|  |  | Curehard MED | 10 | 10 | 10 | 10 | 10 |
|  |  | EPON HPT 1062 |  |  |  |  |  |
|  |  | DDS |  |  |  |  |  |

TABLE 12-continued

|  |  | Product No. | Example 66 | Example 67 | Example 68 | Example 69 | Example 70 |
|---|---|---|---|---|---|---|---|
|  |  | DDM |  |  |  |  |  |
|  |  | 4,4'-DADPE |  |  |  |  |  |
|  |  | m-PDA |  |  |  |  |  |
|  |  | m/p-APA |  |  |  |  |  |
|  |  | MXDA |  |  |  |  |  |
|  | Component (E) | Pyrazole |  |  |  |  |  |
|  |  | 3-Amino-5-tert-butylpyrazole | 0.5 |  |  |  |  |
|  |  | 1-Allyl-3,5-dimethylpyrazole |  | 0.5 |  |  |  |
|  |  | 3-Aminopyrazole |  |  | 0.5 |  |  |
|  |  | 3,5-Dimethylpyrazole |  |  |  | 0.5 |  |
|  |  | 1,2,4-Triazole |  |  |  |  | 0.5 |
|  |  | 4-Amino-1,2,4-triazole |  |  |  |  |  |
|  |  | 1,2,3-Triazole |  |  |  |  |  |
|  |  | 3-Mercapto-1,2,4-triazole |  |  |  |  |  |
|  |  | 1-[N,N-Bis(2-ethylhexyl)aminomethyl]benzotriazole |  |  |  |  |  |
|  |  | 1-[N,N-Bis(2-ethylhexyl)aminomethyl]methylbenzotriazole |  |  |  |  |  |
|  |  | 2,2'-[[(Methyl-1H-benzotriazole-1-yl)methyl]imino]bisethanol |  |  |  |  |  |
|  |  | Benzimidazole |  |  |  |  |  |
|  |  | 1-Methylbenzimidazole |  |  |  |  |  |
|  |  | 1,2-Dimethylimidazole |  |  |  |  |  |
|  |  | 1-Benzyl-2-methylimidazole |  |  |  |  |  |
|  |  | 1-Benzyl-2-phenylimidazole |  |  |  |  |  |
|  |  | 1-Cyanoethyl-2-methylimidazole |  |  |  |  |  |
|  |  | 1-Cyanoethyl-2-ethyl-4-methylimidazole |  |  |  |  |  |
| Evaluation | (1) Viscosity |  | D | D | D | D | D |
|  | (2) Increase in viscosity |  | ○○ | ○○ | ○○ | ○○ | ○○ |
|  | (3) Inkjet dischargeability |  | ○○ | ○ | ○○ | ○○ | ○ |
|  | (4) Wettability/spreadability |  | ○○ | ○○ | ○○ | ○○ | ○○ |
|  | (5) Length of pot life |  | ○○ | ○○ | ○○ | ○○ | ○○ |
|  | (6) Heat resistance |  | ○ | ○ | ○ | ○ | ○ |
|  | (7) Acid resistance |  | ○○ | ○○ | ○○ | ○○ | ○○ |
|  | (8) Insulation reliability (migration resistance) |  | ○ | ○ | ○ | ○ | ○ |
|  | (9) Long-term reliability (cooling/heating cycle resistance evaluation) [500 cycles] |  | ○ | ○ | ○ | ○ | ○ |
|  | (9) Long-term reliability (cooling/heating cycle resistance evaluation) [1000 cycles] |  | ○ | ○ | Δ | Δ | ○ |

TABLE 13

|  |  | Product No. | Example 71 | Example 72 | Example 73 | Example 74 | Example 75 |
|---|---|---|---|---|---|---|---|
| Components to be added (part by weight) | Component (A1), bifunctional or higher | IRR214-K | 70 | 70 | 70 | 70 | 70 |
|  |  | DCP-M |  |  |  |  |  |
|  |  | TMPTA |  |  |  |  |  |
|  |  | EBECRYL135 |  |  |  |  |  |
|  |  | TMPEOTA |  |  |  |  |  |
|  |  | TPGDA |  |  |  |  |  |
|  |  | 1,6-HDDA |  |  |  |  |  |
|  |  | 1,9-NDDA |  |  |  |  |  |
|  |  | NP-A |  |  |  |  |  |
|  |  | 4EG-A |  |  |  |  |  |
|  |  | 9EG-A |  |  |  |  |  |
|  |  | 16EG-A |  |  |  |  |  |
|  |  | MPD-A |  |  |  |  |  |
|  |  | EBECRYL8402 |  |  |  |  |  |
|  |  | EBECRYL4858 |  |  |  |  |  |
|  |  | EBECRYL180 |  |  |  |  |  |
|  | Component (B) | Irgacure 907 | 5 | 5 | 5 | 5 | 5 |
|  |  | Irgacure 369 |  |  |  |  |  |
|  |  | Irgacure 379EG |  |  |  |  |  |
|  |  | TPO |  |  |  |  |  |
|  | Component (C) | YD-127 | 15 | 15 | 15 | 15 | 15 |
|  |  | YDF-170 |  |  |  |  |  |
|  |  | EX-211 |  |  |  |  |  |
|  |  | JER630 |  |  |  |  |  |
|  |  | JER152 |  |  |  |  |  |
|  |  | TETRAD-X |  |  |  |  |  |
|  |  | TETRAD-C |  |  |  |  |  |
|  | Component (D) | EH105L |  |  |  |  |  |
|  |  | DETDA |  |  |  |  |  |
|  |  | Curehard MED | 10 | 10 | 10 | 10 | 10 |
|  |  | EPON HPT 1062 |  |  |  |  |  |
|  |  | DDS |  |  |  |  |  |

TABLE 13-continued

|  |  | Product No. | Example 71 | Example 72 | Example 73 | Example 74 | Example 75 |
|---|---|---|---|---|---|---|---|
|  |  | DDM |  |  |  |  |  |
|  |  | 4,4'-DADPE |  |  |  |  |  |
|  |  | m-PDA |  |  |  |  |  |
|  |  | m/p-APA |  |  |  |  |  |
|  |  | MXDA |  |  |  |  |  |
|  | Component (E) | Pyrazole |  |  |  |  |  |
|  |  | 3-Amino-5-tert-butylpyrazole |  |  |  |  |  |
|  |  | 1-Allyl-3,5-dimethylpyrazole |  |  |  |  |  |
|  |  | 3-Aminopyrazole |  |  |  |  |  |
|  |  | 3,5-Dimethylpyrazole |  |  |  |  |  |
|  |  | 1,2,4-Triazole |  |  |  |  |  |
|  |  | 4-Amino-1,2,4-triazole | 0.5 |  |  |  |  |
|  |  | 1,2,3-Triazole |  | 0.5 |  |  |  |
|  |  | 3-Mercapto-1,2,4-triazole |  |  | 0.5 |  |  |
|  |  | 1-[N,N-Bis(2-ethylhexyl)aminomethyl]benzotriazole |  |  |  | 0.5 |  |
|  |  | 1-[N,N-Bis(2-ethylhexyl)aminomethyl]methylbenzotriazole |  |  |  |  | 0.5 |
|  |  | 2,2'-[[(Methyl-1H-benzotriazole-1-yl)methyl]imino]bisethanol |  |  |  |  |  |
|  |  | Benzimidazole |  |  |  |  |  |
|  |  | 1-Methylbenzimidazole |  |  |  |  |  |
|  |  | 1,2-Dimethylimidazole |  |  |  |  |  |
|  |  | 1-Benzyl-2-methylimidazole |  |  |  |  |  |
|  |  | 1-Benzyl-2-phenylimidazole |  |  |  |  |  |
|  |  | 1-Cyanoethyl-2-methylimidazole |  |  |  |  |  |
|  |  | 1-Cyanoethyl-2-ethyl-4-methylimidazole |  |  |  |  |  |
| Evaluation | (1) Viscosity | | D | D | D | D | D |
|  | (2) Increase in viscosity | | ◯◯ | ◯◯ | ◯◯ | ◯◯ | ◯◯ |
|  | (3) Inkjet dischargeability | | ◯◯ | ◯◯ | ◯◯ | ◯◯ | ◯◯ |
|  | (4) Wettability/spreadability | | ◯◯ | ◯◯ | ◯◯ | ◯◯ | ◯◯ |
|  | (5) Length of pot life | | ◯◯ | ◯◯ | ◯◯ | ◯◯ | ◯◯ |
|  | (6) Heat resistance | | ◯ | ◯ | ◯ | ◯ | ◯ |
|  | (7) Acid resistance | | ◯◯ | ◯◯ | ◯◯ | ◯◯ | ◯◯ |
|  | (8) Insulation reliability (migration resistance) | | ◯ | ◯ | ◯ | ◯ | ◯ |
|  | (9) Long-term reliability (cooling/heating cycle resistance evaluation) [500 cycles] | | ◯ | ◯ | ◯ | ◯ | ◯ |
|  | (9) Long-term reliability (cooling/heating cycle resistance evaluation) [1000 cycles] | | Δ | Δ | Δ | Δ | Δ |

TABLE 14

|  |  | Product No. | Example 76 | Example 77 | Example 78 | Example 79 |
|---|---|---|---|---|---|---|
| Components to be added (part by weight) | Component (A1), bifunctional or higher | IRR214-K | 70 | 70 | 70 | 70 |
|  |  | DCP-M |  |  |  |  |
|  |  | TMPTA |  |  |  |  |
|  |  | EBECRYL135 |  |  |  |  |
|  |  | TMPEOTA |  |  |  |  |
|  |  | TPGDA |  |  |  |  |
|  |  | 1,6-HDDA |  |  |  |  |
|  |  | 1,9-NDDA |  |  |  |  |
|  |  | NP-A |  |  |  |  |
|  |  | 4EG-A |  |  |  |  |
|  |  | 9EG-A |  |  |  |  |
|  |  | 16EG-A |  |  |  |  |
|  |  | MPD-A |  |  |  |  |
|  |  | EBECRYL8402 |  |  |  |  |
|  |  | EBECRYL4858 |  |  |  |  |
|  |  | EBECRYL180 |  |  |  |  |
|  | Component (B) | Irgacure 907 | 5 | 5 | 5 | 5 |
|  |  | Irgacure 369 |  |  |  |  |
|  |  | Irgacure 379EG |  |  |  |  |
|  |  | TPO |  |  |  |  |
|  | Component (C) | YD-127 | 15 | 15 | 15 | 15 |
|  |  | YDF-170 |  |  |  |  |
|  |  | EX-211 |  |  |  |  |
|  |  | JER630 |  |  |  |  |
|  |  | JER152 |  |  |  |  |
|  |  | TETRAD-X |  |  |  |  |
|  |  | TETRAD-C |  |  |  |  |
|  | Component (D) | EH105L |  |  |  |  |
|  |  | DETDA |  |  |  |  |
|  |  | Curehard MED | 10 | 10 | 10 | 10 |
|  |  | EPON HPT 1062 |  |  |  |  |
|  |  | DDS |  |  |  |  |

TABLE 14-continued

|  |  | Product No. | Example 76 | Example 77 | Example 78 | Example 79 |
|---|---|---|---|---|---|---|
|  |  | DDM |  |  |  |  |
|  |  | 4,4'-DADPE |  |  |  |  |
|  |  | m-PDA |  |  |  |  |
|  |  | m/p-APA |  |  |  |  |
|  |  | MXDA |  |  |  |  |
|  | Component (E) | Pyrazole |  |  |  |  |
|  |  | 3-Amino-5-tert-butylpyrazole |  |  |  |  |
|  |  | 1-Allyl-3,5-dimethylpyrazole |  |  |  |  |
|  |  | 3-Aminopyrazole |  |  |  |  |
|  |  | 3,5-Dimethylpyrazole |  |  |  |  |
|  |  | 1,2,4-Triazole |  |  |  |  |
|  |  | 4-Amino-1,2,4-triazole |  |  |  |  |
|  |  | 1,2,3-Triazole |  |  |  |  |
|  |  | 3-Mercapto-1,2,4-triazole |  |  |  |  |
|  |  | 1-[N,N-Bis(2-ethylhexyl)aminomethyl]benzotriazole |  |  |  |  |
|  |  | 1-[N,N-Bis(2-ethylhexyl)aminomethyl]methylbenzotriazole |  |  |  |  |
|  |  | 2,2'-[[(Methyl-1H-benzotriazole-1-yl)methyl]imino]bisethanol | 0.5 |  |  |  |
|  |  | Benzimidazole |  | 0.5 |  |  |
|  |  | 1-Methylbenzimidazole |  |  | 0.5 |  |
|  |  | 1,2-Dimethylimidazole |  |  |  | 0.5 |
|  |  | 1-Benzyl-2-methylimidazole |  |  |  |  |
|  |  | 1-Benzyl-2-phenylimidazole |  |  |  |  |
|  |  | 1-Cyanoethyl-2-methylimidazole |  |  |  |  |
|  |  | 1-Cyanoethyl-2-ethyl-4-methylimidazole |  |  |  |  |
| Evaluation | (1) Viscosity |  | D | D | D | D |
|  | (2) Increase in viscosity |  | ○○ | ○○ | ○○ | ○○ |
|  | (3) Inkjet dischargeability |  | ○○ | ○○ | ○○ | ○○ |
|  | (4) Wettability/spreadability |  | ○○ | ○○ | ○○ | ○○ |
|  | (5) Length of pot life |  | ○○ | ○○ | ○○ | ○○ |
|  | (6) Heat resistance |  | ○ | ○ | ○ | ○ |
|  | (7) Acid resistance |  | ○○ | ○ | ○ | ○ |
|  | (8) Insulation reliability (migration resistance) |  | ○ | ○ | ○ | ○ |
|  | (9) Long-term reliability (cooling/heating cycle resistance evaluation) [500 cycles] |  | ○ | ○ | ○ | ○ |
|  | (9) Long-term reliability (cooling/heating cycle resistance evaluation) [1000 cycles] |  | Δ | Δ | Δ | Δ |

TABLE 15

|  |  | Product No. | Example 80 | Example 81 | Example 82 | Example 83 |
|---|---|---|---|---|---|---|
| Components to be added (part by weight) | Component (A1), bifunctional or higher | IRR214-K | 70 | 70 | 70 | 70 |
|  |  | DCP-M |  |  |  |  |
|  |  | TMPTA |  |  |  |  |
|  |  | EBECRYL135 |  |  |  |  |
|  |  | TMPEOTA |  |  |  |  |
|  |  | TPGDA |  |  |  |  |
|  |  | 1,6-HDDA |  |  |  |  |
|  |  | 1,9-NDDA |  |  |  |  |
|  |  | NP-A |  |  |  |  |
|  |  | 4EG-A |  |  |  |  |
|  |  | 9EG-A |  |  |  |  |
|  |  | 16EG-A |  |  |  |  |
|  |  | MPD-A |  |  |  |  |
|  |  | EBECRYL8402 |  |  |  |  |
|  |  | EBECRYL4858 |  |  |  |  |
|  |  | EBECRYL180 |  |  |  |  |
|  | Component (B) | Irgacure 907 | 5 | 5 | 5 | 5 |
|  |  | Irgacure 369 |  |  |  |  |
|  |  | Irgacure 379EG |  |  |  |  |
|  |  | TPO |  |  |  |  |
|  | Component (C) | YD-127 | 15 | 15 | 15 | 15 |
|  |  | YDF-170 |  |  |  |  |
|  |  | EX-211 |  |  |  |  |
|  |  | JER630 |  |  |  |  |
|  |  | JER152 |  |  |  |  |
|  |  | TETRAD-x |  |  |  |  |
|  |  | TETRAD-C |  |  |  |  |
|  | Component (D) | EH105L |  |  |  |  |
|  |  | DETDA |  |  |  |  |
|  |  | Curehard MED | 10 | 10 | 10 | 10 |
|  |  | EPON HPT 1062 |  |  |  |  |
|  |  | DDS |  |  |  |  |

TABLE 15-continued

|  |  | Product No. | Example 80 | Example 81 | Example 82 | Example 83 |
|---|---|---|---|---|---|---|
|  | Component (E) | DDM | | | | |
|  |  | 4,4'-DADPE | | | | |
|  |  | m-PDA | | | | |
|  |  | m/p-APA | | | | |
|  |  | MXDA | | | | |
|  |  | Pyrazole | | | | |
|  |  | 3-Amino-5-tert-butylpyrazole | | | | |
|  |  | 1-Allyl-3,5-dimethylpyrazole | | | | |
|  |  | 3-Aminopyrazole | | | | |
|  |  | 3,5-Dimethylpyrazole | | | | |
|  |  | 1,2,4-Triazole | | | | |
|  |  | 4-Amino-1,2,4-triazole | | | | |
|  |  | 1,2,3-Triazole | | | | |
|  |  | 3-Mercapto-1,2,4-triazole | | | | |
|  |  | 1-[N,N-Bis(2-ethylhexyl)aminomethyl]benzotriazole | | | | |
|  |  | 1-[N,N-Bis(2-ethylhexyl)aminomethyl]methylbenzotriazole | | | | |
|  |  | 2,2'-[[(Methyl-1H-benzotriazole-1-yl)methyl]imino]bisethanol | | | | |
|  |  | Benzimidazole | | | | |
|  |  | 1-Methylbenzimidazole | | | | |
|  |  | 1,2-Dimethylimidazole | | | | |
|  |  | 1-Benzyl-2-methylimidazole | 0.5 | | | |
|  |  | 1-Benzyl-2-phenylimidazole | | 0.5 | | |
|  |  | 1-Cyanoethyl-2-methylimidazole | | | 0.5 | |
|  |  | 1-Cyanoethyl-2-ethyl-4-methylimidazole | | | | 0.5 |
| Evaluation | (1) Viscosity | | D | D | D | D |
|  | (2) Increase in viscosity | | ⊙⊙ | ⊙⊙ | ⊙⊙ | ⊙⊙ |
|  | (3) Inkjet dischargeability | | ⊙⊙ | ⊙⊙ | ⊙⊙ | ⊙⊙ |
|  | (4) Wettability/spreadability | | ⊙⊙ | ⊙⊙ | ⊙⊙ | ⊙⊙ |
|  | (5) Length of pot life | | ⊙⊙ | ⊙⊙ | ⊙⊙ | ⊙⊙ |
|  | (6) Heat resistance | | ○ | ○ | ○ | ○ |
|  | (7) Acid resistance | | ○ | ○ | ○ | ○ |
|  | (8) Insulation reliability (migration resistance) | | ○ | ○ | ○ | ○ |
|  | (9) Long-term reliability (cooling/heating cycle resistance evaluation) [500 cycles] | | ○ | ○ | ○ | ○ |
|  | (9) Long-term reliability (cooling/heating cycle resistance evaluation) [1000 cycles] | | Δ | Δ | Δ | Δ |

TABLE 16

|  |  | Product No. | Example 84 | Example 85 | Example 86 | Example 87 | Example 88 | Example 89 |
|---|---|---|---|---|---|---|---|---|
| Components to be added (part by weight) | Component (A1), bifunctional or higher | IRR214-K | 70 | 70 | 70 | 70 | 70 | 70 |
|  |  | DCP-M | | | | | | |
|  |  | TMPTA | | | | | | |
|  |  | EBECRYL135 | | | | | | |
|  |  | TMPEOTA | | | | | | |
|  |  | TPGDA | | | | | | |
|  |  | 1,6-HDDA | | | | | | |
|  |  | 1,9-NDDA | | | | | | |
|  |  | NP-A | | | | | | |
|  |  | 4EG-A | | | | | | |
|  |  | 9EG-A | | | | | | |
|  |  | 16EG-A | | | | | | |
|  |  | MPD-A | | | | | | |
|  |  | EBECRYL8402 | | | | | | |
|  |  | EBECRYL4858 | | | | | | |
|  |  | EBECRYL180 | | | | | | |
|  | Component (B) | Irgacure 907 | 5 | 5 | 5 | 5 | 5 | 5 |
|  |  | Irgacure 369 | | | | | | |
|  |  | Irgacure 379EG | | | | | | |
|  |  | TPO | | | | | | |
|  | Component (C) | YD-127 | 15 | 15 | 15 | 15 | 15 | 15 |
|  |  | YDF-170 | | | | | | |
|  |  | EX-211 | | | | | | |
|  |  | JER630 | | | | | | |
|  |  | JER152 | | | | | | |
|  |  | TETRAD-X | | | | | | |
|  |  | TETRAD-C | | | | | | |
|  | Component (D) | EH105L | 10 | 10 | 10 | 10 | 10 | 10 |
|  |  | DETDA | | | | | | |
|  |  | Curehard MED | | | | | | |
|  |  | EPON HPT 1062 | | | | | | |
|  |  | DDS | | | | | | |

TABLE 16-continued

|  |  | Product No. | Example 84 | Example 85 | Example 86 | Example 87 | Example 88 | Example 89 |
|---|---|---|---|---|---|---|---|---|
|  |  | DDM |  |  |  |  |  |  |
|  |  | 4,4'-DADPE |  |  |  |  |  |  |
|  |  | m-PDA |  |  |  |  |  |  |
|  |  | m/p-APA |  |  |  |  |  |  |
|  |  | MXDA |  |  |  |  |  |  |
|  | Solvent (F) | Propylene glycol 1-monomethyl ether 2-acetate | 0.5 | 1 |  |  |  |  |
|  |  | Dipropylene glycol monomethyl ether |  |  | 0.5 | 1 |  |  |
|  |  | Dipropylene glycol dimethyl ether |  |  |  |  | 0.5 | 1 |
|  | Color material (G) | 650M |  |  |  |  |  |  |
|  |  | NUBIAN BLUE PS-5630 |  |  |  |  |  |  |
|  |  | valifast black 3804 |  |  |  |  |  |  |
|  |  | valifast black 1821 |  |  |  |  |  |  |
| Evaluation | (1) Viscosity |  | D | D | D | D | D | D |
|  | (2) Increase in viscosity |  | ⊙⊙ | ⊙⊙ | ⊙⊙ | ⊙⊙ | ⊙⊙ | ⊙⊙ |
|  | (3) Inkjet dischargeability |  | ⊙⊙ | ⊙⊙ | ⊙⊙ | ⊙⊙ | ⊙⊙ | ⊙⊙ |
|  | (4) Wettability/spreadability |  | ⊙⊙ | ⊙⊙ | ⊙⊙ | ⊙⊙ | ⊙⊙ | ⊙⊙ |
|  | (5) Length of pot life |  | ⊙⊙ | ⊙⊙ | ⊙⊙ | ⊙⊙ | ⊙⊙ | ⊙⊙ |
|  | (6) Heat resistance |  | ○ | ○ | ○ | ○ | ○ | ○ |
|  | (7) Acid resistance |  | ○ | ○ | ○ | ○ | ○ | ○ |
|  | (8) Insulation reliability (migration resistance) |  | ○ | ○ | ○ | ○ | ○ | ○ |
|  | (9) Long-term reliability (cooling/heating cycle resistance evaluation) [500 cycles] |  | ○ | ○ | ○ | ○ | ○ | ○ |
|  | (9) Long-term reliability (cooling/heating cycle resistance evaluation) [1000 cycles] |  | Δ | Δ | Δ | Δ | Δ | Δ |

TABLE 17

|  |  | Product No. | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|
| Components to be added (part by weight) | Component (A1), bifunctional or higher | IRR214-K | 70 | 70 | 70 | 70 | 70 | 70 | 70 |
|  |  | DCP-M |  |  |  |  |  |  |  |
|  |  | TMPTA |  |  |  |  |  |  |  |
|  |  | EBECRYL135 |  |  |  |  |  |  |  |
|  |  | TMPEOTA |  |  |  |  |  |  |  |
|  |  | TPGDA |  |  |  |  |  |  |  |
|  |  | 1,6-HDDA |  |  |  |  |  |  |  |
|  |  | 1,9-NDDA |  |  |  |  |  |  |  |
|  |  | NP-A |  |  |  |  |  |  |  |
|  |  | 4EG-A |  |  |  |  |  |  |  |
|  |  | 9EG-A |  |  |  |  |  |  |  |
|  |  | 16EG-A |  |  |  |  |  |  |  |
|  |  | MPD-A |  |  |  |  |  |  |  |
|  |  | EBECRYL8402 |  |  |  |  |  |  |  |
|  |  | EBECRYL4858 |  |  |  |  |  |  |  |
|  |  | EBECRYL180 |  |  |  |  |  |  |  |
|  | Component (B) | Irgacure 907 | 5 | 5 | 5 | 5 | 5 | 5 | 5 |
|  |  | Irgacure 369 |  |  |  |  |  |  |  |
|  |  | Irgacure 379EG |  |  |  |  |  |  |  |
|  |  | TPO |  |  |  |  |  |  |  |
|  | Component (C) | YD-127 | 15 | 15 | 15 | 15 | 15 | 15 | 15 |
|  |  | YDF-170 |  |  |  |  |  |  |  |
|  |  | EX-211 |  |  |  |  |  |  |  |
|  |  | JER630 |  |  |  |  |  |  |  |
|  |  | JER152 |  |  |  |  |  |  |  |
|  |  | TETRAD-X |  |  |  |  |  |  |  |
|  |  | TETRAD-C |  |  |  |  |  |  |  |
|  | Another thermal curing agent | MDA | 10 |  |  |  |  |  |  |
|  |  | IPDA |  | 10 |  |  |  |  |  |
|  |  | Laromin C-260 |  |  | 10 |  |  |  |  |
|  |  | WONDAMINE HM |  |  |  | 10 |  |  |  |
|  |  | 13BAC |  |  |  |  | 10 |  |  |
|  |  | N-AEP |  |  |  |  |  | 10 |  |
|  |  | EPOMATE B-002 |  |  |  |  |  |  | 10 |
| Evaluation | (1) Viscosity |  | D | D | D | D | D | D | D |
|  | (2) Increase in viscosity |  | X | X | X | X | X | X | X |
|  | (3) Inkjet dischargeability |  | X | X | X | X | X | X | X |
|  | (4) Wettability/spreadability |  | ○ | ○ | ○ | ○ | ○ | ○ | ○ |
|  | (5) Length of pot life |  | X | X | X | X | X | X | X |
|  | (6) Heat resistance |  | X | X | X | X | X | X | X |
|  | (7) Acid resistance |  | Δ | Δ | Δ | Δ | Δ | Δ | Δ |

TABLE 17-continued

| Product No. | Comparative Example 1 | Comparative Example 2 | Comparative Example 3 | Comparative Example 4 | Comparative Example 5 | Comparative Example 6 | Comparative Example 7 |
|---|---|---|---|---|---|---|---|
| (8) Insulation reliability (migration resistance) | ○ | ○ | ○ | ○ | ○ | ○ | ○ |
| (9) Long-term reliability (cooling/heating cycle resistance evaluation) [500 cycles] | X | X | X | X | X | X | X |
| (9) Long-term reliability (cooling/heating cycle resistance evaluation) [1000 cycles] | — | — | — | — | — | — | — |

TABLE 18

| | | Product No. | Comparative Example 8 | Comparative Example 9 | Comparative Example 10 | Comparative Example 11 | Comparative Example 12 |
|---|---|---|---|---|---|---|---|
| Components to be added (part by weight) | Component (A2), monofunctional | IBOA | 70 | | | | |
| | | FA-513AS | | 70 | | | |
| | | FA-511AS | | | 70 | | |
| | | 2HEA | | | | 70 | |
| | | ODA-L | | | | | 70 |
| | Component (B) | Irgacure 907 | 5 | 5 | 5 | 5 | 5 |
| | | Irgacure 369 | | | | | |
| | | Irgacure 379EG | | | | | |
| | | TPO | | | | | |
| | Component (C) | YD-127 | 15 | 15 | 15 | 15 | 15 |
| | | YDF-170 | | | | | |
| | | EX-211 | | | | | |
| | | JER630 | | | | | |
| | | JER152 | | | | | |
| | | TETRAD-X | | | | | |
| | | TETRAD-C | | | | | |
| | Component (D) | EH105L | 10 | 10 | 10 | 10 | 10 |
| | | DETDA | | | | | |
| | | Curehard MED | | | | | |
| | | EPON HPT 1062 | | | | | |
| | | DDS | | | | | |
| | | DDM | | | | | |
| | | 4,4'-DADPE | | | | | |
| | | m-PDA | | | | | |
| | | m/p-APA | | | | | |
| | | MXDA | | | | | |
| Evaluation | (1) Viscosity | | D | D | D | D | D |
| | (2) Increase in viscosity | | X | X | X | X | X |
| | (3) Inkjet dischargeability | | X | X | X | X | X |
| | (4) Wettability/spreadability | | ○ | ○ | ○ | ○ | ○ |
| | (5) Length of pot life | | X | X | X | X | X |
| | (6) Heat resistance | | X | X | X | X | X |
| | (7) Acid resistance | | X | X | X | X | X |
| | (8) Insulation reliability (migration resistance) | | ○ | ○ | ○ | ○ | ○ |
| | (9) Long-term reliability (cooling/heating cycle resistance evaluation) [500 cycles] | | X | X | X | X | X |
| | (9) Long-term reliability (cooling/heating cycle resistance evaluation) [1000 cycles] | | — | — | — | — | — |

The invention claimed is:
1. A curable composition for inkjet which is applied with an inkjet device upon use and is irradiated with light to make the curing thereof proceed and is subsequently cured by heating upon use,
the curable composition comprising a photocurable compound, a thermally curable compound, a photopolymerization initiator and a thermal curing agent, and containing no solvent or containing a solvent,
the content of the solvent being 1% by weight or less in 100% by weight of the curable composition for inkjet when the curable composition contains the solvent,
the photocurable compound containing a polyfunctional compound having at least two (meth)acryloyl groups, and
the thermal curing agent being an aromatic amine having at least one benzene ring and at least two amino groups wherein the curable composition for inkjet is capable of being discharged from a nozzle of the inkjet device, and
wherein the viscosity of the curable composition as measured before heating at 25° C. in accordance with JIS K2283 is 160 to 1200 mPa·s inclusive.

2. The curable composition for inkjet according to claim 1, wherein the aromatic amine is an aromatic amine represented by formula (1) or formula (2) shown below:

[Chemical formula 1]

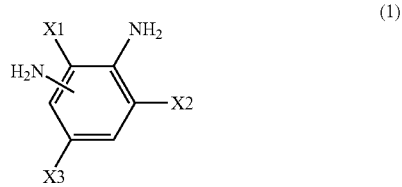

(1)

wherein X1, X2 and X3 independently represent an alkyl group having 1 to 6 carbon atoms or an SCH$_3$ group; and

[Chemical formula 2]

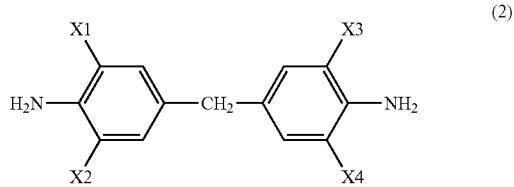

(2)

wherein X1, X2, X3 and X4 independently represent an alkyl group having 1 to 6 carbon atoms or an SCH$_3$ group.

3. The curable composition for inkjet according to claim 1, wherein the curable composition further contains an aromatic heterocyclic compound having a 5-membered ring having a nitrogen atom.

4. The curable composition for inkjet according to claim 3, wherein the aromatic heterocyclic compound is a compound represented by formula (3) formula (4) or formula (5) shown below

[Chemical formula 3]

(3)

[Chemical formula 4]

(4)

[Chemical formula 5]

(5)

5. The curable composition for inkjet according to claim 1, wherein the ratio of the viscosity of the curable composition as measured after heating at 80° C. for 24 hours under an oxygen-free environment to the viscosity of the curable composition as measured before heating is 1.1 or less.

6. The curable composition for inkjet according to claim 1, wherein the curable composition contains a color material.

7. A method for manufacturing an electronic component, comprising the steps of:
applying a curable composition for inkjet as recited in claim 1 by an inkjet mode to draw a pattern with the curable composition; and
irradiating the pattern-shaped curable composition for inkjet with light and then applying heat to the pattern-shaped curable composition to cure the pattern-shaped curable composition, thereby forming a cured product layer.

8. An inkjet printer filled with a curable composition for inkjet, wherein
the inkjet primer has an inkjet head which has a nozzle,
the curable composition for inkjet is capable of being discharged from the nozzle,
the curable composition comprises a photocurable compound, a thermally curable compound, a photopolymerization initiator and a thermal curing agent, and contains no solvent or contains a solvent,
the content of the solvent is 1% by weight or less in 100% by weight of the curable composition for inkjet when the curable composition contains the solvent,
the photocurable compound contains a polyfunctional compound having at least two (meth)acryloyl groups,
the thermal curing agent is an aromatic amine having at least one benzene ring and at least two amino groups, and
the viscosity of the curable composition as measured before heating at 25° C. in accordance with JIS K2283 is 160 to 1200 mPa·s inclusive.

9. The inkjet printer according to claim 8, wherein the aromatic amine is an aromatic amine represented by formula (1) or formula (2) shown below:

[Chemical formula 1]

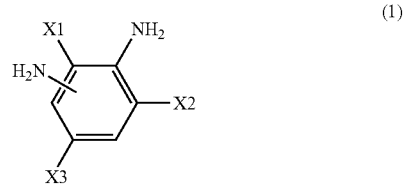

(1)

wherein X1, X2 and X3 independently represent alkyl group having 1 to 6 carbon atoms or an SCH$_3$ group; and

[Chemical formula 2]

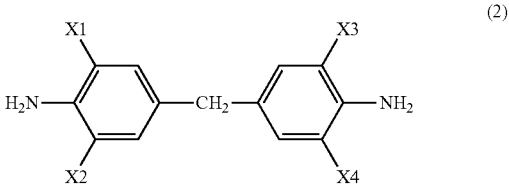

(2)

wherein X1, X2, X3 and X4 independently represent an alkyl group having 1 to 6 carbon atoms or an $SCH_3$ group.

10. The inkjet printer according to claim 8, wherein the curable composition further contains an aromatic heterocyclic compound having a 5-membered ring having a nitrogen atom.

11. The inkjet printer according to claim 10, wherein the aromatic heterocyclic compound is a compound represented by formula (3), formula (4) or formula (5) shown below

[Chemical formula 3]

(3)

[Chemical formula 4]

(4)

[Chemical formula 5]

(5)

12. The inkjet printer according to claim 8, wherein the ratio of the viscosity of the curable composition as measured after heating at 80° C. for 24 hours under an oxygen-free environment to the above-mentioned viscosity of the curable composition as measured before heating is 1.1 or less.

13. The inkjet printer according to claim 8, wherein the curable composition contains a color material.

14. A method for manufacturing an electronic component, comprising the steps of:
applying the curable composition for inkjet from the nozzle of the inkjet printer filled with the curable composition for inkjet as recited in claim 8 by an inkjet mode to draw a pattern with the curable composition; and
irradiating the pattern-shaped curable composition for inkjet with light and then applying heat to the pattern-shaped curable composition to cure the pattern-shaped curable composition, thereby forming a cured product layer which has a drawn pattern-shape.

15. The inkjet printer according to claim 8, wherein the inkjet printer is provided with a warming unit for warming the inside of the inkjet head to 50° C. or higher.

16. The method for manufacturing an electronic component according to claim 14, wherein the inkjet printer is provided with a warming unit for warming the inside of the inkjet device or the inside of the inkjet head to 50° C. or higher, and
when the curable composition for inkjet is applied, the inside of the inkjet head is warmed to 50° C. or higher by the warming unit.

* * * * *